(12) United States Patent
Amara et al.

(10) Patent No.: US 10,449,517 B2
(45) Date of Patent: Oct. 22, 2019

(54) HIGH SURFACE AREA FIBER MEDIA WITH NANO-FIBRILLATED SURFACE FEATURES

(71) Applicant: EMD Millipore Corporation, Burlington, MA (US)

(72) Inventors: John Paul Amara, Burlington, MA (US); John Boyle, Burlington, MA (US); David Yavorsky, Burlington, MA (US); Benjamin Cacace, Burlington, MA (US)

(73) Assignee: EMD Millipore Corporation, Burlington, MA (US)

( * ) Notice: Subject to any disclaimer, the term of this patent is extended or adjusted under 35 U.S.C. 154(b) by 148 days.

(21) Appl. No.: 15/323,471

(22) PCT Filed: Aug. 19, 2015

(86) PCT No.: PCT/US2015/045873
§ 371 (c)(1),
(2) Date: Jan. 3, 2017

(87) PCT Pub. No.: WO2016/036508
PCT Pub. Date: Mar. 10, 2016

(65) Prior Publication Data
US 2017/0165638 A1    Jun. 15, 2017

Related U.S. Application Data

(60) Provisional application No. 62/044,630, filed on Sep. 2, 2014.

(51) Int. Cl.
*B01J 20/285* (2006.01)
*B01D 15/32* (2006.01)
(Continued)

(52) U.S. Cl.
CPC .......... *B01J 20/285* (2013.01); *B01D 15/327* (2013.01); *B01D 15/361* (2013.01);
(Continued)

(58) Field of Classification Search
CPC ........ B01D 15/00; B01D 15/08; B01D 15/20; B01D 15/26; B01D 15/38; B01D 15/3804;
(Continued)

(56) References Cited

U.S. PATENT DOCUMENTS 3,382,305 A    5/1968  Breen
3,936,394 A    2/1976  Kusunose et al.
(Continued)

FOREIGN PATENT DOCUMENTS

CN    101036876 A    9/2007
CN    101617072 A    12/2009
(Continued)

OTHER PUBLICATIONS

Bruss et al., "Topological Defects, Surface Geometry and Cohesive Energy of Twisted Filament Bundles," Soft Matter, vol. 9, Issued 34, pp. 8327-8345, 2013.
(Continued)

*Primary Examiner* — Katherine Zalasky
(74) *Attorney, Agent, or Firm* — Nields, Lemack & Frame, LLC

(57) ABSTRACT

Chromatography media including a high surface area thermoplastic porous nanofiber and an ion-exchange ligand functionality on the surface of the fiber. The porous nanofibers display a convoluted structure that is comprised of discrete bundles of highly entangled nanofibrils that may be fibrillated or ridged. The porous fibers can be prepared through the extraction of a dissolvable mineral or polymeric
(Continued)

porogen that is embedded into the fiber during its manufacture in a melt extrusion process.

11 Claims, 12 Drawing Sheets

(51) Int. Cl.
    *B01J 20/26* (2006.01)
    *B01J 20/28* (2006.01)
    *B01J 20/281* (2006.01)
    *B01J 20/32* (2006.01)
    *C07K 1/16* (2006.01)
    *B01D 15/36* (2006.01)
    *B01D 15/38* (2006.01)
    *B01J 39/19* (2017.01)
    *B01J 47/127* (2017.01)
    *B01J 41/13* (2017.01)
    *C12N 7/00* (2006.01)
    *B01J 39/26* (2006.01)
    *B01J 41/20* (2006.01)
    *C07K 1/18* (2006.01)
    *C07K 1/20* (2006.01)
    *C07K 1/22* (2006.01)

(52) U.S. Cl.
    CPC ......... *B01D 15/362* (2013.01); *B01D 15/363* (2013.01); *B01D 15/3804* (2013.01); *B01D 15/3809* (2013.01); *B01J 20/26* (2013.01); *B01J 20/281* (2013.01); *B01J 20/28007* (2013.01); *B01J 20/28023* (2013.01); *B01J 20/28028* (2013.01); *B01J 20/3208* (2013.01); *B01J 20/3278* (2013.01); *B01J 20/3293* (2013.01); *B01J 39/19* (2017.01); *B01J 39/26* (2013.01); *B01J 41/13* (2017.01); *B01J 41/20* (2017.01); *B01J 47/127* (2017.01); *C07K 1/16* (2013.01); *C07K 1/18* (2013.01); *C07K 1/20* (2013.01); *C07K 1/22* (2013.01); *C12N 7/00* (2013.01)

(58) Field of Classification Search
    CPC ............. B01D 15/3809; B01D 15/363; B01D 15/362; B01D 15/361; B01D 15/327; B01D 15/42; B01D 15/424; G01N 30/02; G01N 30/48; G01N 30/482; B01J 20/285; B01J 20/26; B01J 20/28007; B01J 20/28023; B01J 20/28028; B01J 20/281; B01J 20/28033; B01J 20/28038; B01J 20/28042; B01J 20/28054; B01J 20/282; B01J 47/127; B01J 41/13; C12N 7/00; C12N 7/02; C12N 7/025
    See application file for complete search history.

(56) References Cited

U.S. PATENT DOCUMENTS

| | | | |
|---|---|---|---|
| 4,169,790 A | 10/1979 | Pretorius et al. | |
| 4,384,957 A | 5/1983 | Crowder et al. | |
| 4,512,897 A | 4/1985 | Crowder et al. | |
| 4,657,742 A | 4/1987 | Beaver | |
| 4,675,104 A | 6/1987 | Rai et al. | |
| 4,721,572 A | 1/1988 | Jordan | |
| 5,162,074 A | 11/1992 | Hills | |
| 5,360,540 A | 11/1994 | Andelman | |
| 5,468,847 A | 11/1995 | Heilmann et al. | |
| 5,502,022 A | 3/1996 | Schwarz et al. | |
| 5,800,706 A | 9/1998 | Fischer | |
| 5,886,154 A | 3/1999 | Lebing et al. | |
| 5,906,747 A | 5/1999 | Coffman et al. | |
| 5,948,528 A | 9/1999 | Helms et al. | |
| 6,001,889 A | 12/1999 | Lefebvre | |
| 6,008,036 A | 12/1999 | Fanget et al. | |
| 6,099,960 A | 8/2000 | Tennent et al. | |
| 6,099,965 A * | 8/2000 | Tennent | B01J 20/20 264/29.1 |
| 6,228,995 B1 | 5/2001 | Lee | |
| 6,254,883 B1 | 7/2001 | Jarnstrom et al. | |
| 6,736,973 B1 | 5/2004 | Podgornik et al. | |
| 6,811,874 B2 | 11/2004 | Tanaka et al. | |
| 7,026,154 B1 | 4/2006 | Gaillac et al. | |
| 7,291,263 B2 | 11/2007 | Ward et al. | |
| 7,311,825 B2 | 12/2007 | Shah | |
| 7,374,673 B2 | 5/2008 | Marcus | |
| 7,465,397 B2 | 12/2008 | Siwak et al. | |
| 7,510,848 B2 | 3/2009 | Hammond et al. | |
| 7,517,381 B2 | 4/2009 | Rohrbach et al. | |
| 8,129,019 B2 | 3/2012 | Pourdeyhimi et al. | |
| 8,137,561 B2 | 3/2012 | Kozlov et al. | |
| 8,536,288 B2 | 9/2013 | Furumoto et al. | |
| 8,722,757 B2 | 5/2014 | Janke et al. | |
| 9,029,517 B2 | 5/2015 | Yavorsky et al. | |
| 9,284,663 B2 * | 3/2016 | Pourdeyhimi | D01F 6/00 |
| 9,815,050 B2 | 11/2017 | Yavorsky et al. | |
| 2002/0037565 A1 | 3/2002 | Blanche et al. | |
| 2002/0050470 A1 | 5/2002 | Jinno et al. | |
| 2002/0058625 A1 | 5/2002 | Mitterer et al. | |
| 2002/0177693 A1 | 11/2002 | Lebing et al. | |
| 2003/0127393 A1 | 7/2003 | Tepper et al. | |
| 2003/0146156 A1 | 8/2003 | Siwak et al. | |
| 2003/0180936 A1 * | 9/2003 | Memarzadeh | A61K 48/0091 435/239 |
| 2005/0023221 A1 | 2/2005 | Marcus | |
| 2005/0072737 A1 | 4/2005 | Ward et al. | |
| 2005/0080251 A1 | 4/2005 | Lemmens | |
| 2005/0260911 A1 | 11/2005 | Ochi et al. | |
| 2006/0003073 A1 | 1/2006 | Etzel et al. | |
| 2006/0032816 A1 | 2/2006 | Marcus et al. | |
| 2006/0070950 A1 | 4/2006 | Rasmussen et al. | |
| 2006/0073527 A1 | 4/2006 | Albitar et al. | |
| 2006/0275781 A1 | 12/2006 | Pham et al. | |
| 2007/0102363 A1 | 5/2007 | Little et al. | |
| 2008/0105612 A1 | 5/2008 | Chappas | |
| 2008/0108265 A1 | 5/2008 | Pourdeyhimi et al. | |
| 2009/0130738 A1 | 5/2009 | Kozlov | |
| 2009/0176052 A1 | 7/2009 | Childs et al. | |
| 2010/0047904 A1 | 2/2010 | Forde et al. | |
| 2010/0058542 A1 | 3/2010 | Kourda et al. | |
| 2010/0136025 A1 | 6/2010 | Hickman et al. | |
| 2010/0176051 A1 | 7/2010 | Shimagaki | |
| 2010/0311850 A1 | 12/2010 | Wickert et al. | |
| 2010/0330119 A1 | 12/2010 | Yamamoto et al. | |
| 2011/0033633 A1 * | 2/2011 | Bothof | B01J 20/285 427/496 |
| 2011/0076771 A1 | 3/2011 | Gabriele et al. | |
| 2011/0142863 A1 | 6/2011 | Iyer et al. | |
| 2011/0165645 A1 | 7/2011 | Xiong | |
| 2012/0021796 A1 | 1/2012 | Coulombe | |
| 2012/0029176 A1 | 2/2012 | Yavorsky et al. | |
| 2012/0074611 A1 | 3/2012 | Zhou et al. | |
| 2012/0074612 A1 | 3/2012 | Scrivens et al. | |
| 2012/0077249 A1 * | 3/2012 | Ramaswamy | C12N 7/00 435/239 |
| 2012/0077404 A1 | 3/2012 | Scrivens et al. | |
| 2012/0077405 A1 | 3/2012 | Zhou et al. | |
| 2012/0077406 A1 | 3/2012 | Scrivens et al. | |
| 2012/0148841 A1 | 6/2012 | Pourdeyhimi et al. | |
| 2012/0193278 A1 | 8/2012 | Kozlov et al. | |
| 2013/0112625 A1 * | 5/2013 | Bahukudumbi | B01J 20/28007 210/660 |
| 2013/0115837 A1 | 5/2013 | Kitchen et al. | |
| 2013/0245139 A1 * | 9/2013 | Kozlov | C07K 1/22 521/27 |
| 2014/0296464 A1 * | 10/2014 | Bracewell | B01D 15/361 526/317.1 |
| 2015/0258540 A1 | 9/2015 | Yavorsky et al. | |
| 2015/0352465 A1 | 12/2015 | Amara et al. | |

(56) References Cited

U.S. PATENT DOCUMENTS

| | | | |
|---|---|---|---|
| 2017/0298091 | A1 | 10/2017 | Stone et al. |
| 2018/0085743 | A1 | 3/2018 | Yavorsky et al. |

FOREIGN PATENT DOCUMENTS

| | | | |
|---|---|---|---|
| CN | 101768206 | A | 7/2010 |
| CN | 103153423 | A | 6/2013 |
| EP | 0269462 | A2 | 6/1988 |
| EP | 1141249 | A1 | 10/2001 |
| EP | 1796807 | A2 | 6/2007 |
| EP | 2036584 | A1 | 3/2009 |
| EP | 2087153 | A2 | 8/2009 |
| EP | 2089563 | A2 | 8/2009 |
| EP | 2266675 | A2 | 12/2010 |
| EP | 2336304 | A1 | 6/2011 |
| EP | 2346897 | A2 | 7/2011 |
| EP | 2266675 | A3 | 9/2011 |
| EP | 2727930 | A1 | 5/2014 |
| EP | 2883882 | A1 | 6/2015 |
| JP | 62-4440 | A | 1/1987 |
| JP | 5-239709 | A | 9/1993 |
| JP | 8-108069 | A | 4/1996 |
| JP | 8-170958 | A | 7/1996 |
| JP | 11-279945 | A | 10/1999 |
| JP | 2000-504002 | A | 4/2000 |
| JP | 2000-510201 | A | 8/2000 |
| JP | 2003-524157 | A | 8/2003 |
| JP | 2008-510142 | A | 4/2008 |
| JP | 2010-509099 | A | 3/2010 |
| JP | 2011-128147 | A | 6/2011 |
| JP | 2013-535683 | A | 9/2013 |
| JP | 2013-539787 | A | 10/2013 |
| JP | 2014-512340 | A | 5/2014 |
| KR | 10-0522108 | B1 | 1/2006 |
| KR | 10-2009-0102745 | A | 9/2009 |
| KR | 10-2013-0031351 | A | 3/2013 |
| WO | 93/10899 | A2 | 6/1993 |
| WO | 97/27844 | A1 | 8/1997 |
| WO | 99/34916 | A1 | 7/1999 |
| WO | 99/44053 | A2 | 9/1999 |
| WO | 00/40702 | A1 | 7/2000 |
| WO | 01/92552 | A2 | 12/2001 |
| WO | 02/083893 | A2 | 10/2002 |
| WO | 03/027366 | A1 | 4/2003 |
| WO | 2005/011849 | A2 | 2/2005 |
| WO | 2005/021844 | A2 | 3/2005 |
| WO | 2006/020640 | A2 | 2/2006 |
| WO | 2008/006780 | A1 | 1/2008 |
| WO | 2008/039136 | A1 | 4/2008 |
| WO | 2008/057426 | A2 | 5/2008 |
| WO | 2008/057431 | A2 | 5/2008 |
| WO | 2009/146321 | A1 | 12/2009 |
| WO | 2009/151593 | A1 | 12/2009 |
| WO | 2010/036774 | A1 | 4/2010 |
| WO | 2010/048192 | A2 | 4/2010 |
| WO | 2016/093926 | A1 | 6/2010 |
| WO | 2010/072381 | A1 | 7/2010 |
| WO | 2010/096704 | A2 | 8/2010 |
| WO | 2012/015908 | A2 | 2/2012 |
| WO | 2012/044382 | A1 | 4/2012 |
| WO | 2012/051147 | A2 | 4/2012 |
| WO | 2012/068442 | A1 | 5/2012 |
| WO | 2012/141791 | A1 | 10/2012 |
| WO | 2013/002330 | A1 | 1/2013 |
| WO | 2013/068603 | A2 | 5/2013 |
| WO | 2014/024514 | A1 | 2/2014 |
| WO | 2014/120387 | A1 | 8/2014 |
| WO | 2014/126575 | A1 | 8/2014 |
| WO | 2014/129964 | A2 | 8/2014 |

OTHER PUBLICATIONS

Office action dated Sep. 19, 2017 in co-pending U.S. Appl. No. 14/759,426.
Japanese communication, with English translation, dated Mar. 27, 2018 in corresponding Japanese patent application No. 2017-511980.
International Search Report and Written Opinion dated Apr. 12, 2015 in co-pending PCT application No. PCT/US2015/053140.
Office action dated Mar. 27, 2017 in co-pending U.S. Appl. No. 14/682,456 (MCA-1262/1).
International Preliminary Report on Patentability dated Jun. 22, 2017 in co-pending PCT application No. PCT/US2015/053140.
Chinese communication, with English translation, dated Jun. 23, 2017 in co-pending Chinese patent application No. 201380021431.X (MCA-1262-China).
Brunazzi et al., "An Economical Criterion for Packed Absorption Column Design," Chemical and Biochemical Engineering Quarterly, 15 (4), pp. 199-206, 2002.
Schure et al., "Simulation of Ordered Packed Beds in Chromatography," Journal of Chromatography A, vol. 1031, pp. 79-85, 2004.
Canadian communication dated Nov. 29, 2018 in co-pending Canadian patent application No. 2,966,515.
GE Healthcare, "Strategies for Protein Purification, Handbook", 2010.
Final rejection dated Dec. 17, 2018 in co-pending U.S. Appl. No. 15/677,526 (MCA-1262/2).
Office action dated Jun. 8, 2018 in co-pending U.S. Appl. No. 15/677,526 (MCA-1262/2).
Korean communication, with English translation, dated Dec. 1, 2017 in corresponding Korean patent application No. 10-2017-7000772.
Notice of allowance dated Jul. 28, 2017 in co-pending U.S. Appl. No. 14/682,456 (MCA-1262/1).
European communication dated Apr. 12, 2018 in corresponding European patent application No. 15838269.7.
Japanese communication, with English translation, dated Jul. 17, 2017 in co-pending Japanese patent application No. 2017-530167.
Korean communication, with English translation, dated Jul. 30, 2018 in corresponding Korean patent application No. 10-2017-7000772.
Amara et al, "New Disposable Technology for the Chromatographic Purification of Biopharmaceuticals", 245th ACS National Meeting and Exposition, Apr. 7, 2013, Divisions, Pub #45.
Kawai et al., "Protein Binding to Polymer Brush, Based on Ion-Exchange, Hydrophobic, and Affinity Interactions", Journal of Chromatography B, vol. 790, pp. 131-142, 2003.
Chinese communication, with English translation, dated Jul. 27, 2018 in corresponding Chinese patent application No. 201580047255.6.
European communication dated Jun. 19, 2017 in co-pending European patent application No. 11813102.8 (MCA-1262-Europe).
International Search Report and Written Opinion dated Apr. 6, 2012 in co-pending PCT application No. PCT/US2011/045519 (MCA-1262-PCT).
International Preliminary Report on Patentability dated Feb. 14, 2013 in co-pending PCT application No. PCT/US2011/045519 (MCA-1262-PCT).
International Search Report and Written Opinion dated Apr. 8, 2014 in co-pending PCT application No. PCT/US14/10158.
International Search Report and Written Opinion dated Nov. 5, 2015 in corresponding PCT application No. PCT/US15/45873.
International Preliminary Report on Patentability dated Mar. 16, 2017 in corresponding PCT application No. PCT/US2015/045873.
Chinese communication, with English translation, dated Apr. 14, 2014 in co-pending Chinese patent application No. CN 201180037517.2 (MCA 1262 China).
Chinese communication, with English translation, dated Jun. 2, 2016 in co-pending Chinese patent application No. 201480006972.X.
Chinese communication, with English translation, dated Dec. 5, 2016 in co-pending Chinese patent application No. 201180037517.2 (MCA-1262-China).
Japanese Communication, with English translation, dated Jan. 7, 2014 in co-pending Japanese patent application No. JP 2013-523201 (MCA-1262PCT-Japan).

(56) References Cited

OTHER PUBLICATIONS

Japanese communication, with English translation, dispatched Jan. 6, 2015 in co-pending Japanese patent application No. 2013-523201 (MCA-1262PCT-Japan).
Japanese communication, with English translation, dated May 10, 2016 in co-pending Japanese patent application No. 2015-135562 (MCA-1262/1-Japan).
Japanese communication, with English translation, dated Aug. 30, 2016 in co-pending Japanese patent application No. 2015-556020.
Korean communication, with English translation, dated Dec. 1, 2014 in co-pending Korean patent application 10-2014-7025710 (MCA-1262-Korea-Div2).
Korean communication, with English translation, dated Jan. 29, 2016 in co-pending Korean patent application No. 10-2015-7002666.
Asher et al, "Technical Report No. 47 Preparation of Virus Spikes Used for Virus Clearance Studies", Parenteral Drug Association, 2010.
Berns et al., Chapter 65, "Parvoviridae," in Fields, Fields Virology, 2007.
Bolton et al, "Normal-flow virus filtration: detection and assessment of the endpoint in bioprocessing", Biotechnology and Applied Biochemistry, vol. 42, Issue 2, Oct. 2005, Abstract.
Brorson, "Phages used as alternatives for mammalian viruses", Powerpoint Presentation.
Brorson et al, "Characterization and purification of bacteriophages using chromatofocusing", Journal of Chromatography A, vol. 1207, Issues 1-2, Oct. 2008, pp. 110-121.
Chahal et al, "Primary Recovery and Chromatographic Purification of Adeno-associated Virus Type 2 Produced by Baculovirus/Insect Cell System," Journal of Virological Methods, vol. 139, pp. 61-70, 2007.
Cauhan, Principles of Biochemistry and Biophysics, 1st Edition, University Science Press, New Delhi, 2008, p. 31, Introduction to the Concepts of Chemistry.
Coi et al, "Characterization of non-uniformly charged ion-exchange membranes prepared by plasma-induced graft polymerization", Journal of Membrane Science, vol. 268, Issue 2, Jan. 2006, pp. 165-174.
Clayden, et al., Organic Chemistry, 1st Edition, Oxford University Press: Oxford, 2001, pp. 203-204, Neutral oxygen bases.
Hamaker et al., "Transport Properties of Rolled, Continuous Stationary Phase Columns," Biotechnology Progress, vol. 14, pp. 21-30, 1998.
Marcus et al., "Capillary-Channeled Polymer Fibers as Stationary Phases in Liquid Chromatography Separations," Journal of Chromatography A, vol. 986, pp. 17-31, 2003.
Miesegaes et al, "Viral Clearance by Flow-Through Mode Ion Exchange Columns and Membrane Adsorbers", Biotechnology Progress, vol. 30, Issue 1, 2014, pp. 124-131.
Müller et al, "Geosynthetics in geoenvironmental engineering", Science and Technology of Advanced Materials, vol. 16, No. 3, May 2015.
Koo, et al., AAPS PharmSciTech, vol. 12, No. 2, Jun. 2011, pp. 746-754, "Investigation into Stability of Poly(Vinyl Alcohol)-Based Opadry II Films".
Rowland et al., "Pore Structure Analysis of Purified, Sodium Hydroxide-Treated and Liquid Ammonia-Treated cotton Celluloses," Journal of Applied Polymer Science, vol. 29, pp. 3349-3357, 1984.
Stanelle et al., "Hydrodynamic flow in capillary-channel fiber columns for liquid chromatography", Journal of Chromatography A, vol. 1100, 2005, pp. 68-75.
Wang, et al., Biotechnol. Prog. 2003, vol. 19, No. 2, pp. 464-468, "Recovery of Acinetobacter radioresistens Lipase by Hydrophobic Adsorption to n-Hexadecane Coated on Nonwoven Fabric".
Zhu Ping, "Functional Fibers and Functional Textiles," China Textile & Apparel Press, 1st Edition, p. 218, Aug. 2006.
U.S. Appl. No. 61/415,605, "High-Surface Area Fibers and Nonwoven Membranes for Use in Bioseparations", 35 pages, filed Nov. 19, 2010 by Gurgel, et al.
"Technical Report No. 41 Virus Filtration", PDA Journal of Pharmaceutical Science and Technology, vol. 59, 2005.
Evans et al., Evans pKa Table, 2005.
Office action dated Sep. 18, 2015 in co-pending U.S. Appl. No. 14/682,456 (MCA-1262/1).
Final rejection dated Mar. 15, 2016 in co-pending U.S. Appl. No. 14/682,456 (MCA-1262/1).
Office action dated Jul. 28, 2016 in co-pending U.S. Appl. No. 14/682,456 (MCA-1262/1).
Final rejection dated Nov. 10, 2016 in co-pending U.S. Appl. No. 14/682,456 (MCA-1262/1).
Office action dated Nov. 15, 2016 in co-pending U.S. Appl. No. 14/759,426.
Final rejection dated Mar. 27, 2017 in co-pending U.S. Appl. No. 14/759,426.
Japanese communication, with English translation, dated May 14, 2019 in co-pending Japanese patent application No. 2017-530167.
Office action dated Apr. 17, 2019 in co-pending U.S. Appl. No. 15/677,526 (MCA-1262/2).
Office action dated Mar. 13, 2019 in co-pending U.S. Appl. No. 15/521,428.
Office action dated Jun. 13, 2019 in co-pending U.S. Appl. No. 15/521,428.

* cited by examiner

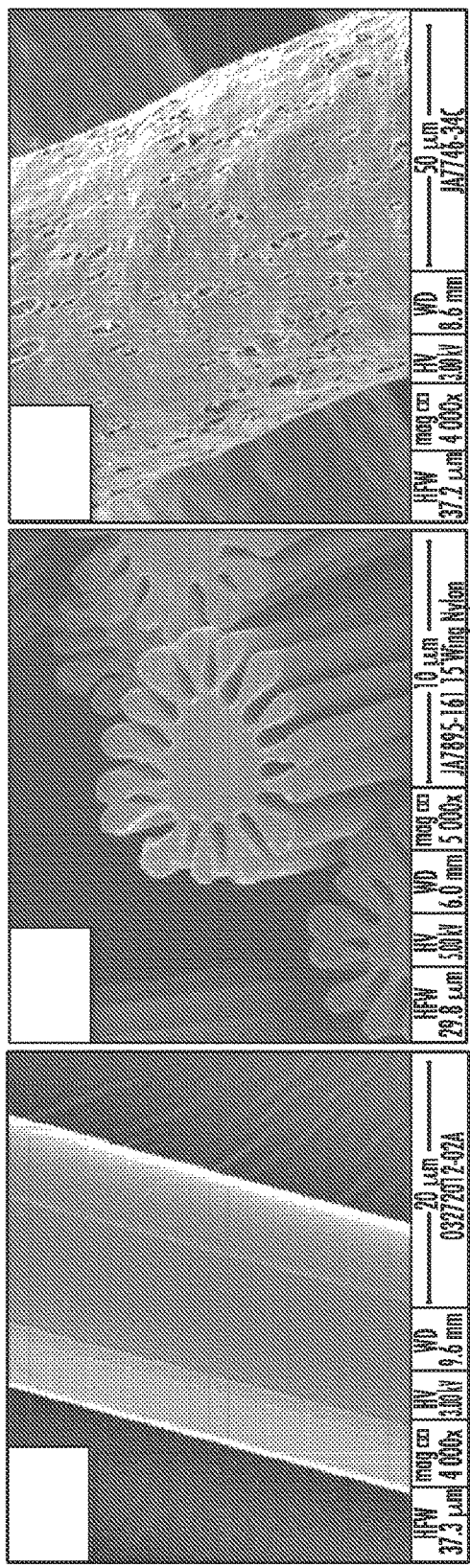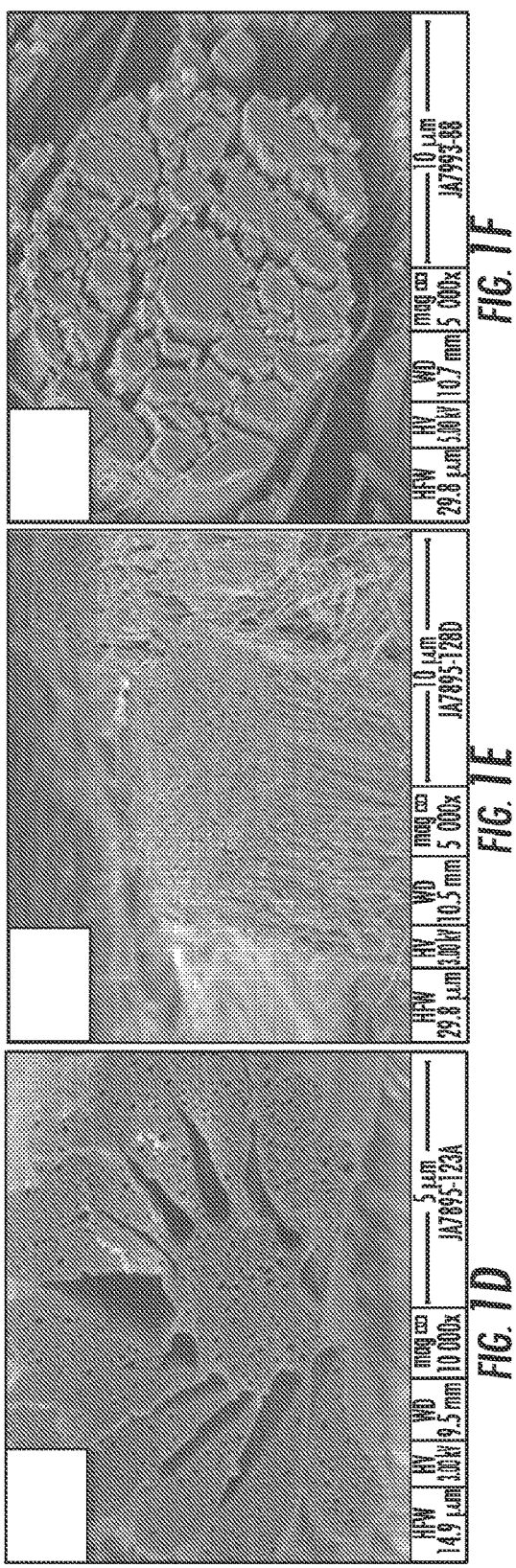

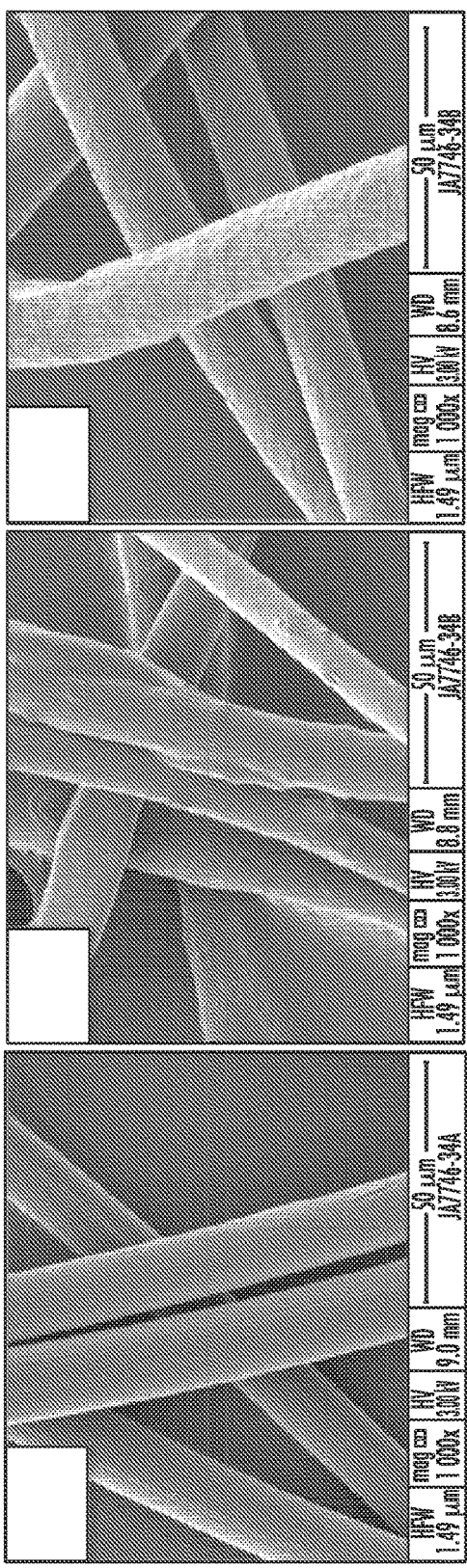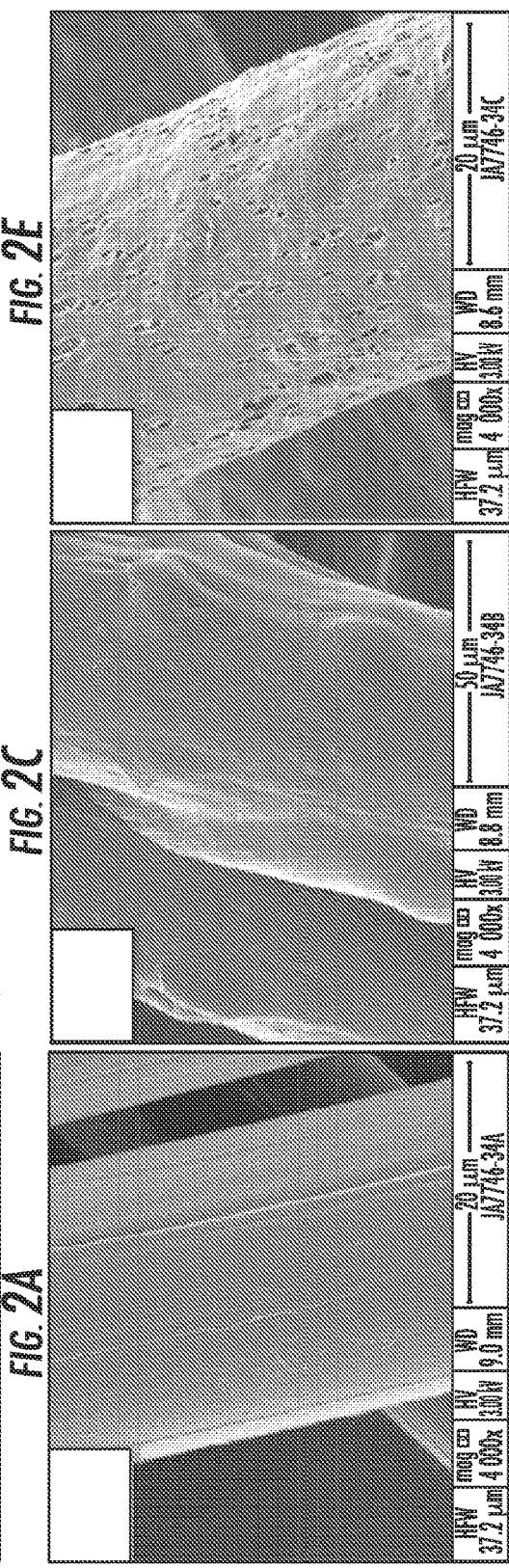
FIG. 2A  FIG. 2C  FIG. 2E
FIG. 2B  FIG. 2D  FIG. 2F

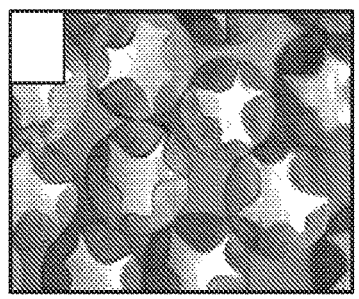 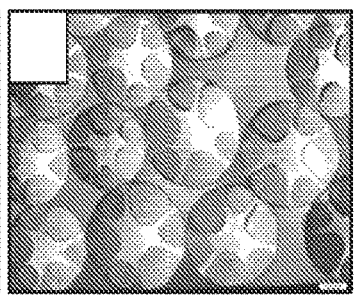 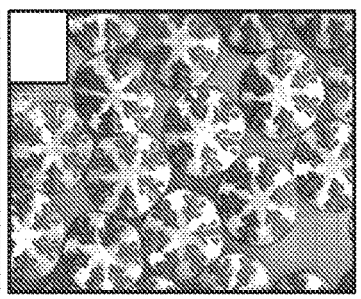
FIG. 13A  FIG. 13B  FIG. 13C
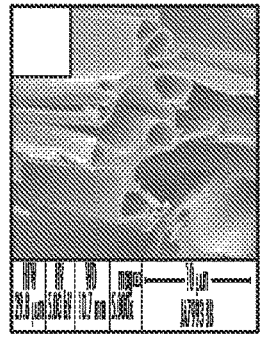 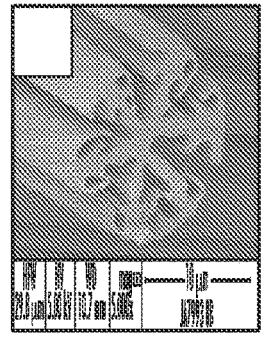
FIG. 13D  FIG. 13E

HIGH SURFACE AREA FIBER MEDIA WITH NANO-FIBRILLATED SURFACE FEATURES

This application claims priority of U.S. Provisional Application Ser. No. 62/044,630 filed Sep. 2, 2014, the disclosure of which is incorporated herein by reference.

FIELD

Embodiments disclosed herein relate to porous, high surface area fibers that are suitable for service as a chromatographic stationary phase for the bind/elute purification of proteins in a cation exchange chromatography mode, for example.

BACKGROUND

The commercial scale purification of various therapeutic biomolecules, such as monoclonal antibodies, is currently accomplished using bead-based chromatography resins. Monoclonal antibodies continue to gain importance as therapeutic and diagnostic agents. The process of screening hybridoma libraries for candidate mAbs is both time consuming and labor intensive. Once a hybridoma cell line expressing a suitable mAb is established, a purification methodology must be developed to produce sufficient mAb for further characterization. A traditional method for purifying involves using Protein A or Protein G affinity chromatography, as well as ion exchange chromatography. The purified antibody is desalted and exchanged into a biological buffer using dialysis. The entire process typically requires several days to complete and can be particularly onerous if multiple mAbs are to be evaluated in parallel.

Chromatography resins are currently prepared with various ligand structures that enable the beads to function in affinity, cation-exchange, or anion-exchange modes. These resins demonstrate a high porosity and large surface areas that provide materials with sufficient adsorptive capacities for the batch processing of biomolecules at production scales (e.g., 10,000 liters). Chromatography resins typically present a spherical structure that enables an efficient column packing with minimal flow non-uniformities. The interstitial spaces between the beads provide flow channels for convective transport through the chromatography column. This enables chromatography columns to be run with large bed depths at a high linear velocity with a minimal pressure drop. The combination of these factors enables chromatography resins to present the required efficiency, high permeability, and sufficient binding capacity that are required for the large-scale purification of biomolecules.

In bead-based chromatography, most of the available surface area for adsorption is internal to the bead. Consequently, the separation process is inherently slow since the rate of mass transport is typically controlled by pore diffusion. To minimize this diffusional resistance and concomitantly maximize dynamic binding capacity, small diameter beads can be employed. However, the use of small diameter beads comes at the price of increased column pressure drop. Consequently, the optimization of preparative chromatographic separations often involves a compromise between efficiency/dynamic capacity (small beads favored) and column pressure drop (large beads favored).

Chromatography media typically has a very high cost (>$1000/L) and significant quantities are required for large scale production columns. As a result, biopharmaceutical manufacturers recycle chromatography resins hundreds of times. Each of these regeneration cycles consumes substantial quantities of buffer media, and each step incurs additional costs associated with the validation of each cleaning, sterilization, and column packing operation.

Several technologies are described in the patent literature and marketed commercially for biopharmaceutical separations based on functionalized fibrous media and/or composites. Most rely on incorporating a porous gel into the fiber matrix, the gel providing the needed surface area to gain reasonable binding capacities. However, in such constructions, poor uniformity in gel location and mass generally leads to poor efficiencies (shallow breakthrough and elution fronts). In addition, resistance to flow can be high even for short bed depths, a problem often aggravated by gel compression under modest pressure loads. Another approach taken has been the incorporation of particulates within the fiber matrix, the particulates often porous and possessing a native adsorptive functionality, examples being activated carbon and silica gel.

Recently, EMD Millipore has developed a fiber based chromatography media for biomolecule purification applications that utilizes a surface-functionalized winged fiber as the adsorptive media. The winged projections on the fiber surface afford a much higher surface area than ordinary round fibers of similar dimensions. The resulting surface functionalized fiber media also has a much higher protein binding capacity than similarly functionalized fibers which lack such winged projections.

Other emerging technologies are currently in development for protein purification applications and these include membrane adsorbers, monoliths, and flow-through adsorber purification methods using commercial resin systems. While membrane adsorbers and monoliths may provide acceptable binding capacities for these applications, these technologies typically have their own scale limitations and the extremely high cost of such purification media may further limit their adoption into a price sensitive industry with an existing purification process template.

SUMMARY

In order to address many of the limitations of the purification technologies currently known in the art, embodiments disclosed herein relate to chromatography media that comprises a low-cost, high surface area thermoplastic fiber and an ion-exchange ligand functionality on the surface of that fiber. In certain embodiments, the ion-exchange ligand is capable of selectively binding proteins from a biological feed stream. The bound protein can be subsequently released from the chromatography media upon a change in the solution conditions, for example, through the use of an elution buffer with a higher ionic strength. In certain embodiments, surface pendant functional groups are added to the media that provides cation-exchange or anion-exchange functionality to the high surface area fibers. This pendant functionality is useful for the ion-exchange chromatographic purification of biomolecules, such as recombinant fusion proteins, Fc containing proteins, ADC's (antibody drug conjugates, vaccines, plasma protein (IgM, blood clotting factors, etc.), and monoclonal antibodies (mAbs).

In certain embodiments the fiber-based stationary phase is porous and displays a convoluted structure that is comprised of discrete bundles of highly entangled nanofibrils. In certain embodiments, each of the nanofibrils located within said nanofibril bundle have diameters less than or equal to 1 micron. These fibers typically present a surface area in the range of 1 to 12 square meters per gram. In certain embodiments, the porous fibers are fibrillated or ridged.

In certain embodiments, the nanofiber bundles may be prepared by the melt extrusion of a blend of two immiscible polymers such as nylon, including polyamide 6, polyamide 6,6, polyamide 4,6, polyamide, polyamide 12, polyamide 6,12, and copolymers or blends of various polyamides, and poly(lactic acid), PLA. After melt extrusion, the fibers are drawn to a target diameter of approximately 20 microns. The PLA polymer porogen component is subsequently extracted by treatment with sodium hydroxide solution, leaving elongated cavities or channels throughout the nylon microfiber. The resulting fiber media has the appearance of a bundle of highly entangled nylon nanofibers that are loosely aligned in a collinear arrangement. These bundles possess the flow properties of ordinary microfibers and also demonstrate a high permeability in a packed bed format. In contrast, individual nanofibers that are not bundled demonstrate a very low permeability in a packed bed format. This unique arrangement of nanofibers provides a high permeability, high surface area substrate that enables a high protein binding capacity after surface modification with the appropriate ion exchange ligand. Fibers modified with a pendant ion-exchange functionality are useful for the chromatographic purification of proteins, such as monoclonal antibodies.

In certain embodiments, a surface area enhanced (SAE) fiber is modified with surface-functional sulfopropyl (SP) ligands and is used in a bind/elute cation exchange chromatography application for the purification of IgG. The SAE fiber media can be surface modified to install pendant ion exchange ligands such as sulfopropyl (SP) groups. The functionalized media can be packed into a suitable device, such as a chromatography column and compressed to a target packing density. A protein solution to be purified can be subsequently passed through this fiber packing, whereupon the protein of interest may bind to ligands on the surface of the SAE fibers through an ion exchange process. For example, at pH 5, the sulfopropyl groups are strongly negatively charged and will bind proteins, such as IgG, whose pI is greater than about 7. After binding of the target protein (e.g., IgG), the column is typically washed with a suitable buffer, such as 50 mM acetate buffer (pH 5) to clear any unbound impurities. Afterwards, the ionic strength of the buffer is increased such as with a 0.5 M sodium chloride/50 mM acetate (pH 5) solution to elute the bound IgG from the SAE fiber column. The fiber column may then be regenerated by washing, such as with 5-10 column volumes of 0.5 M sodium hydroxide and 5-10 column volumes of 50 mM acetate buffer (pH 5). The SAE fiber media is now ready for another CEX bind/elute cycle. Accordingly, embodiments disclosed herein relate to methods for the isolation, purification or separation of biomolecules with media comprising a high surface area functionalized porous fiber.

BRIEF DESCRIPTION OF THE DRAWINGS

FIG. 1(a) is an SEM image of an ordinary non-porous nylon monofilament, 20 micron fiber diameter, at 4000× magnification, in accordance with certain embodiments;

FIG. 1(b) is an SEM image of a 15 wing nylon fiber after complete removal of sheath materials, 15 micron fiber diameter, at 5000× magnification, in accordance with certain embodiments;

FIG. 1(c) is an SEM image of an extruded monofilament with blend composition PA6/Albafil® CaCO$_3$ 75/25 after complete removal of embedded porogens and sheath materials, 2:1 draw ratio, at 4000× magnification, in accordance with certain embodiments;

FIG. 1(d) is a cryo-SEM cross-sectional image after complete removal of embedded porogens and sheath materials, of a 15 wing fiber with core blend composition nylon/PLA 70/30, at 10,000× magnification, in accordance with certain embodiments;

FIG. 1(e) is a cryo-SEM cross-sectional image after complete removal of embedded porogens and sheath materials, of a surface area enhanced (SAE) core/sheath fiber with core blend composition nylon/PLA 60/40, at 5000× magnification, in accordance with certain embodiments;

FIG. 1(f) is a cryo-SEM cross-sectional image after complete removal of embedded porogens and sheath materials, of a "connected islands in the sea" (CIST) fiber with "island" composition PA6 nylon 100/0, "sea" composition PA6 nylon/PLA 55/45, i/S ratio, 1/1, at 5000× magnification, in accordance with certain embodiments;

FIG. 2(a) is an SEM image of extruded monofilaments of PA6 nylon, 2:1 draw ratio, 1000× magnification, in accordance with certain embodiments;

FIG. 2(b) is an SEM image of extruded monofilaments of PA6 nylon, 2:1 draw ratio, 4000× magnification, in accordance with certain embodiments;

FIG. 2(c) is an SEM image after mineral porogen extraction from extruded monofilaments with a blend composition of PA6/Multifex-MM™ CaCO$_3$ 75/25, 1.3:1 draw ratio, 1000× magnification, in accordance with certain embodiments;

FIG. 2(d) is an SEM image after mineral porogen extraction from extruded monofilaments with a blend composition of PA6/Multifex-MM™ CaCO$_3$ 75/25, 1.3:1 draw ratio, 4000× magnification, in accordance with certain embodiments;

FIG. 2(e) is an SEM image after mineral porogen extraction from extruded monofilaments with a blend composition of PA6/Albafil® CaCO$_3$ 75/25, 2:1 draw ratio, 1000× magnification, in accordance with certain embodiments;

FIG. 2(f) is an SEM image after mineral porogen extraction from extruded monofilaments with a blend composition of PA6/Albafil® CaCO$_3$ 75/25, 2:1 draw ratio, 4000× magnification, in accordance with certain embodiments;

FIG. 13(a) is an optical micrograph of fractal fiber 1 in accordance with certain embodiments;

FIG. 13(b) is an optical micrograph of fractal fiber 2 in accordance with certain embodiments;

FIG. 13(c) is an optical micrograph of a snowflake fiber in accordance with certain embodiments;

FIG. 13(d) is an SEM micrograph of fractal fiber 2 in accordance with certain embodiments; and FIG. 13(e) is an SEM micrograph of a snowflake fiber in accordance with certain embodiments.

DETAILED DESCRIPTION

Figures 3A, 3B:
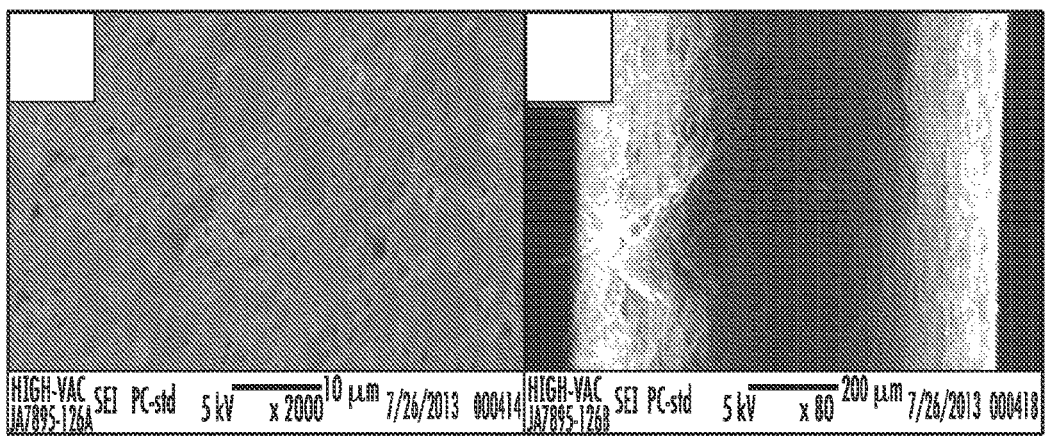
FIG. 3(a) is an SEM image after polymeric porogen extraction from extruded compounded filaments (compounding extruder) with a blend composition of nylon/PLA 65/35, 2000× magnification, in accordance with certain embodiments.
FIG. 3(b) is an SEM image after polymeric porogen extraction from extruded compounded filaments (compounding extruder) with a blend composition of nylon/PLA 60/40, 80× magnification, in accordance with certain embodiments.

Embodiments disclosed herein include high surface area fibers that are suitable for the bind/elute purification of proteins. The fibers are porous and can be prepared through the extraction of a dissolvable mineral or polymeric porogen that is embedded into the fiber during its manufacture in a melt extrusion process. Dissolvable mineral porogens may include precipitated calcium carbonate, silica gel, or any other dissolvable solid mineral particulate. An example of a dissolvable polymeric porogen is poly(lactic acid), PLA. This polymer will dissolve in aqueous sodium hydroxide solution, for example. Dissolvable polymeric porogens may be incorporated into the fiber at loadings ranging between 10 and 90 wt %, with preferred loadings ranging between 35 and 60 wt %. Dissolvable polymeric porogen loadings less than about 25 wt % provide only minimal enhancement of fiber surface area and these fibers also lack the desired porous or fibrillated surface features after porogen extraction. Dissolvable polymeric porogen loadings higher than about 65 wt % may compromise the structural integrity of the fiber after porogen extraction. Dissolvable mineral porogens may be incorporated into the fiber at loadings ranging between 5 and 40 wt %, with preferred loadings ranging between 15 and 25 wt %. Dissolvable mineral porogen loadings less than about 15 wt % provide only minimal enhancement of fiber surface area and these fibers also lack the desired porous surface features after porogen extraction. Dissolvable mineral porogen loadings higher than about 30 wt % may compromise the structural integrity of the fiber during extrusion or after porogen extraction. Loading may be measured via the preprocessing dry weight of the different materials to be introduced into the extruder, or by comparing fiber weight pre and post-porogen removal.

Suitable materials for the fibers include nylon PA6, although any other melt-processable thermoplastic polymers may be used, such as polyamides, polyolefins, polyvinyl chloride, polystyrene, poly methyl methacrylate, polylactic acid, copolymers, polypropylene, polyester, polyethylene terephthalate, polybutylene terephthalate, polyethylene, or thermoplastic urethanes, polyetherurethanes, polyvinyl alcohol, polyimide, polycarbonate, polyetheretherketone, polystyrene, polysulfone, polytrimethylene terephthalate, copolyesters, or liquid crystalline polymers. These thermoplastics may be obtained as pellets or powders and these materials may be subsequently processed into the product fibers by means of a commercial melt compounding and fiber melt extrusion processing equipment. These fibers present a much higher surface area than ordinary round microfibers or winged fibers as illustrated in FIGS. 1a and 1b, respectively. In certain embodiments, the fibers may be surface modified to install the appropriate pendant cation exchange ligand functionality for the bind/elute or flow-through purification of proteins, monoclonal antibodies, or other biomolecules of interest. Suitable ligands that may be deployed on the fiber surfaces include sulfopropyl groups for cation exchange chromatography applications, tetraalkylammonium halides, primary amines, and secondary amines for anion exchange chromatography applications, and n-alkyl chains, phenyl, benzyl, or other aromatic groups for reverse phase chromatography and hydrophobic interaction chromatography applications. The ligands may be installed onto the fiber surfaces by ceric redox grafting polymerizations, ATRP, RAFT, or free radical polymerizations initiated by e-beam, UV, or gamma radiation sources.

In certain embodiments, a suitable thermoplastic polymer is blended with one or more suitable porogen additives, such as with a compounding extruder. The polymer and/or porogen can be pre-dried and dry blended. The blend can then be introduced into an extruder, from which it can be extruded out of a single strand die into a water bath and then pelletized. Alternatively, the base polymer and porogen pellets or powders can be dry blended and fed directly to a fiber or filament spinning machine without pre-compounding. The pellets can then be melt spun into bi-component filaments using an appropriately equipped fiber spinning machine. The blended base polymer/porogen material forms the core and the porogen polymer forms the outer sheath. After fiber spinning, drawing and winding, the porogen can be extracted from the bi-component filaments with a suitable extracting agent such as a 1 M hydrochloric acid solution or 1.5 N sodium hydroxide solution, depending upon the nature of the porogen used.

In FIG. 1c thru 1f, several examples are shown of the high surface area fibers in accordance with certain embodiments. FIG. 1c is a surface SEM image of a porous microfiber prepared using a dissolvable mineral porogen approach. This extruded monofilament was prepared from a melt compounded blend of nylon and 25 wt % precipitated calcium carbonate (Albafil® PCC). After fiber spinning, drawing, and extraction of the calcium carbonate porogen with hydrochloric acid, numerous pores are observable on the surface of the fiber. Kr BET surface area measurement indicates an approximately 300% gain in BET surface area for this material over an ordinary non-porous nylon fiber of approximately the same fiber diameter.

FIG. 1d shows a cryo-SEM cross sectional image of a porous 15 wing fiber prepared using a dissolvable polymeric porogen approach. This extruded bi-component fiber was prepared from a melt compounded blend of nylon and 30 wt % PLA that constitutes the winged fiber core and a dissolvable PLA sheath the surrounds the fiber core and stabilizes the winged projections during melt-spinning (not shown). After fiber spinning, drawing, and extraction of the PLA polymeric porogen from the fiber sheath and from within the fiber core with sodium hydroxide solution, numerous pores are observable throughout the cross-section of the winged fiber.

FIG. 1e shows a cryo-SEM cross sectional image of a porous core/sheath fiber prepared using a dissolvable polymeric porogen approach. This fiber architecture is referred to as a surface area enhanced (SAE) type fiber. This extruded bi-component fiber was prepared from a melt compounded blend of nylon and 40 wt % PLA that constitutes the fiber core and a dissolvable PLA sheath the surrounds the fiber core and stabilizes the material during melt-spinning (not shown). After fiber spinning, drawing, and extraction of the PLA polymeric porogen from the fiber sheath and from within the fiber core with sodium hydroxide solution, a bundled arrangement of loosely-aligned nylon nanofibrils is observed throughout the cross-section of the SAE fiber. This surface area enhanced architecture greatly increases the fiber surface area and Kr BET surface area measurements indicate that values as high as 10.6 $m^2/g$ are achievable by this approach. In contrast, a non-porous, 15 wing fiber has a modest surface area of only 1.4 $m^2/g$.

FIG. 1f shows a cryo-SEM cross sectional image of another type of porous bi-component fiber prepared using a dissolvable polymeric porogen approach. This fiber architecture is referred to as a 'connected islands in the sea' (CIST) type fiber. This extruded bi-component fiber was prepared from a melt compounded blend of nylon and 45 wt % PLA that constitutes the fiber 'sea' domain and an array of 36 continuous nylon 'islands'. After fiber spinning, drawing, and extraction of the PLA polymeric porogen from the fiber 'sea' domain with sodium hydroxide solution, an arrangement of loosely-aligned nylon nanofibrils and larger micron-sized nylon islands are observed throughout the cross-section of the CIST fiber. This 'connected islands in the sea' architecture greatly increases the fiber surface area and $N_2$ BET surface area measurements indicate that values as high as 7 $m^2/g$ are achievable by this approach.

In certain embodiments, the porous fibers disclosed herein may have regularly or irregularly shaped cross-sections. Exemplary shapes include circular, elliptical and polygonal, as well as a winged-shape wherein a central body has a plurality of radial protrusions extending therefrom. In certain embodiments, the fiber cross-section is generally winged-shaped, with a middle region comprising a longitudinal axis that runs down the center of the fiber and having a plurality of projections that extend outwardly from the middle region. In certain embodiments, a plurality of the projections extends generally radially from the middle region. As a result of this configuration, a plurality of channels is defined by the projections. Suitable channel widths between projections range from about 200 to about 1000 nanometers. Suitable fibers are disclosed in U.S. Patent Publication No. 2008/0105612, the disclosure of which is incorporated herein by reference. In certain embodiments, the fibers are fractal fibers having at least three branched projections extending from a longitudinal axis, as shown in FIG. 13(a). In certain embodiments, the fibers are fractal fibers having at least three branched projections extending from a longitudinal axis, each branched projection having sub-projections extending therefrom, as shown in FIGS. 13(b) and (d). In certain embodiments, the fibers are snowflake fibers, having at least six projections extending from a longitudinal axis, each of the projections having at least four sub-projections extending therefrom, as shown in FIGS. 13(c) and (e).

In certain embodiments the high surface area fibers that are suitable for the bind/elute purification of proteins are solid fibers with different shaped cross-sections. These shaped fibers with ion-exchange ligands exhibit sufficient surface area and acceptable flow properties to be used in chromatographic separations. These shaped fibers have surface areas between 0.5 and 5 square meters per gram by BET gas adsorption. The fibers are produced as bi-component fibers. The sheath material is removed exposing the high surface area core. This core is modified with ion-exchange ligands and used in protein separations. Examples of cross sections that can be used are shown in FIG. 13.

The surface functionalization of the high surface area porous fibers can be carried out by the deposition of an epoxy-functional polymer coating onto the fiber surface, followed by heating to covalently attach the polymer coating to the fiber surface, and a subsequent epoxy-ring opening process to install sulfonic acid functionality onto the fiber surface, for example.

In other embodiments, modification of SAE type fibers with a surface-grafted ion exchange ligand for bind/elute cation exchange chromatography applications can be carried out. Activation of the SAE fiber surface with a crosslinked HPA/MBAm 95/5 polymer coating to provide a highly reactive hydroxy-functional coating on the fiber surface may be carried out, followed by a ceric ion redox polymerization, such as with 2-acrylamido-2-methyl-1-propanesulfonic acid sodium salt, to provide a polymer grafted fiber substrate.

A suitable column packing density of between about 0.1 to 0.4 g/ml, preferably about 0.35 g/ml, will provide sufficient flow uniformity for acceptable performance in a chromatographic evaluation.

In certain embodiments, the media (functionalized packed fibers) may be delivered to the user in a prepacked format, unlike bead-based media. The fibers can be fused either by thermal or chemical means to form a semi-rigid structure that can be housed in a pressure vessel. By such a construction, the media and accompanying device can be made ready-to-use. Chromatographic bead-based media is generally delivered as loose material (wet) wherein the user is required is load a pressure vessel (column) and by various means create a well-packed bed without voids or channels. Follow-up testing is generally required to ensure uniformity of packing. In contrast, in accordance with certain embodiments, no packing is required by the user as the product arrives ready for service.

The surface functionalized porous fiber media of the embodiments disclosed herein demonstrates a high permeability in a packed bed format. Depending on the packing density, the bed permeability can range from 2500 mDarcy to less than 100 mDarcy. The packed fiber bed does not compress at high linear velocity.

The surface area enhanced fiber media of embodiments disclosed herein may be configured into a packed bed format within a suitable housing, such as a chromatography column or other device. Packed fiber beds of surface area enhanced staple fibers may be prepared by loading a dilute aqueous suspension of the staple fibers into a chromatography column and a subsequent axial compression of the top solvent distribution header of the chromatography column to a target bed depth of between 1 and 10 cm. Axial compression is defined as the reduction of the bed depth of a staple fiber packing located within a chromatography column or other suitable housing in order to increase the packing density of the staple fiber packing to a target value of between 0.1 and 0.4 g/mL. This compression is accomplished by the mechanical displacement of flow distribution headers to provide a smaller column or device volume and a corresponding increase in chromatography media packing density. In this context, the axis that is being compressed is the vertical axis of the column in which the staple fibers are packed. Since the staple fibers are compressible, the packing density of the staple fibers is correspondingly increased when such an axial compression is performed. In contrast, radial compression is defined as the reduction of the internal diameter of a staple fiber packing within a chromatography column or other suitable housing in order to increase the packing density of the staple fiber packing to a target value of between 0.1 and 0.4 g/mL. Radial compression operations do not change the bed depth of the fiber media packing.

EXAMPLES

Example 1. Melt Compounding with Mineral or Polymeric Porogens

In this experiment, nylon was blended with a variety of mineral or polymeric porogen additives such as calcium carbonate, silica, or poly(lactic acid) polymer (PLA). Ternary mixtures of nylon, mineral and PLA polymer porogens were also prepared. These blends were subsequently used for fiber extrusion experiments.

Several blends of nylon 6 and mineral fillers were made using a compounding extruder. Additional blends were also prepared containing a ternary mixture of nylon, PLA and mineral porogens. Four different types of mineral fillers were examined: Albafil A-O-255-12 from SMI, Vicality Heavy from SMI, Multifex-MM™ from SMI, and Syloid 244FP from W.R. Grace. The pre-dried materials were weighed and dry blended. The dry blend was put onto the feed conveyor which was adjusted to sufficiently feed the microtruder. The material was extruded out of a single strand die into a water bath and then pelletized. Certain nylon/porogen formulations employed in this work are summarized in Table 1 below.

TABLE 1

Summary of nylon formulations compounded with various mineral and polymeric porogens.

| Materials | Blend Ratio | Porogen Type |
| --- | --- | --- |
| PA6:Albafil | 75:25 | Mineral ($CaCO_3$) |
| PA6:Vicality | 75:25 | Mineral ($CaCO_3$) |
| PA6:Syloid | 75:25 | Mineral ($SiO_2$) |
| PA6:Multifex-MM ™ | 75:25 | Mineral ($CaCO_3$) |
| PA6:PLA | 75:25 | Polymer (PLA) |
| PA6:PLA:Albafil | 65:25:10 | Mineral ($CaCO_3$) + Polymer (PLA) |
| PA6:PLA:Vicality | 65:25:10 | Mineral ($CaCO_3$) + Polymer (PLA) |
| PA6:PLA:Syloid | 73.1:24.4:2.5 | Mineral ($SiO_2$) + Polymer (PLA) |

Example 2. Melt Extrusion of Mineral Porogen Loaded Monofilaments

In this experiment, a general description of the process for melt-spinning the blended nylon/mineral porogen pellets into monofilament fibers of approximately 20 micron diameters is provided.

The blended nylon/mineral porogen pellets were melt spun into monofilaments using a fiber spinning machine. The fiber spinning machine is an LBS System from Hills Inc. (Melbourne, Fla.). The extruded monofilament fiber samples were drawn to a diameter of approximately 20 microns. After fiber spinning, drawing and winding, the mineral porogen was subsequently extracted from the monofilaments according to the procedure described below.

Example 3. Mineral Porogen Extraction from Extruded Monofilaments

In this experiment, the process for mineral porogen extraction from extruded monofilament fibers using a 1 M hydrochloric acid solution is described. The fibers are subsequently neutralized, washed, and the surfaces of the fibers are inspected by scanning electron microscopy (SEM). Kr BET surface area measurements are also conducted.

Into a 100 mL glass jar with cap were added 1.0 g of extruded monofilament (approximately 20 μm diameter) and 50 mL of 1.0 M HCl (50 mmol). The suspension was agitated at 30° C. overnight. The fiber solids were isolated by vacuum filtration and washed with 0.5 M Tris-HCl (1×100 mL), DI water (1×100 mL) and ethanol (1×100 mL). The material was placed in an oven to dry at 40° C. for 18 hours. The results of the mineral porogen extraction experiments are shown in Table 2 below. SEM inspection of the fiber surface morphology was conducted after extraction of the mineral porogens and these images are shown in the FIG. 2. The Albafil®-containing monofilament affords large micron-sized pores or cavities on the fiber surfaces after porogen extraction. Due to the smaller particle size of the Multifex-MM™-porogen (<0.2 microns), much smaller pores are observed on the fiber surface after porogen extraction. No such pores are evident on a similarly-treated nylon fiber control sample. Kr BET surface area measurements reveal a significant gain (~300%) in BET surface area for the material prepared using the Albafil® porogen over the non-porous nylon fiber control sample.

TABLE 2

Calcium carbonate mineral porogen extraction.

| Sample ID | Fiber amt (g) | monofilament blend composition (nylon:mineral) | Obtained | % yield (expected yield) | Kr BET Surface area |
|---|---|---|---|---|---|
| 7746-34A | 0.46 g | PA6 (100:0) | 0.44 g | 96% (100%) | 0.12 m$^2$/g |
| 7746-34B | 0.92 g | PA6:Multifex-MM ™ CaCO$_3$ 75:25 | 0.68 g | 74% (75%) | — |
| 7746-34C | 0.61 g | PA6:Albafil CaCO$_3$ 75:25 | 0.47 g | 77% (75%) | 0.33 m$^2$/g |

Example 4. Melt Compounding with Polymeric Porogens

In this experiment, nylon was blended with various amounts of a polymeric porogen, poly(lactic acid) polymer. These blends were subsequently used for fiber extrusion experiments.

A variety of nylon/PLA blend samples were generated using a compounding extruder. A range of PLA and Nylon 6 blends were made and are shown in Table 3 below. The appropriate amount of dried pellets were weighed and dry blended. The dry blended mixture was then added to the feed conveyor belt on the compounding extruder. The feed belt was adjusted to sufficiently feed the compounding extruder. The material was extruded out of a single strand die into a water bath and then pelletized.

TABLE 3

Summary of nylon formulations compounded with PLA as a polymeric porogen.

| Materials | Blend Ratio |
|---|---|
| PA6:PLA | 80:20 |
| PA6:PLA | 75:25 |
| PA6:PLA | 70:30 |
| PA6:PLA | 65:35 |
| PA6:PLA | 60:40 |
| PA6:PLA | 55:45 |
| PA6:PLA | 50:50 |

Example 5. PLA Porogen Extraction from Extruded Filaments

In this experiment, the process for PLA porogen extraction from extruded filaments from the melt compounder using a 1.5 N sodium hydroxide solution is described. The fibers are subsequently neutralized, washed, a gravimetric assay is performed, and the surfaces of the fibers are inspected by scanning electron microscopy (SEM).

Figures 3C, 3D:
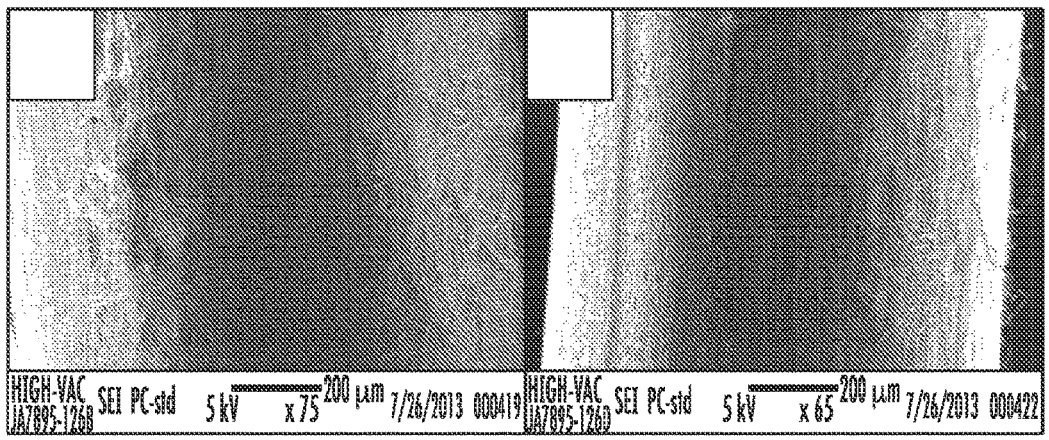
FIG. 3(c) is an SEM image after polymeric porogen extraction from extruded compounded filaments (compounding extruder) with a blend composition of nylon/PLA 55/45, 75× magnification, in accordance with certain embodiments.
FIG. 3(d) is an SEM image after polymeric porogen extraction from extruded compounded filaments (compounding extruder) with a blend composition of nylon/PLA 50/50, 65× magnification, in accordance with certain embodiments.

Into a 250 mL glass jar with cap were added 2.0 g of extruded filament (approximately 2.0 mm diameter) and 0.2 L of 1.5 N NaOH (0.75 mol). The suspension was stirred at room temperature overnight. The fiber solids were isolated by vacuum filtration and washed with DI water (3×250 mL) and ethanol (1×250 mL). The material was placed in an oven to dry at 60° C. for 3 hours. The results of the PLA polymeric porogen extraction experiments from the extruded 2 mm filaments are shown in Table 4 below. From these data, it can be seen that the PLA porogen is more easily extracted for the high PLA loading sample (50 wt % PLA) than it is for the low PLA loading sample (35 wt % PLA). The large difference between the actual and expected yields is due to restricted access to the interior of these large 2 mm diameter filaments. SEM inspection of the filament surface morphology was conducted after extraction of the PLA polymeric porogen and these images are shown in FIG. 3. These data show the appearance of a fibrillated surface morphology after PLA porogen extraction from the filaments. These surface features are quite pronounced for PLA loadings equal to or greater than 40 wt %. Fibrillated surface morphologies such as these are expected to greatly increase the surface area of a fiber substrate.

TABLE 4

PLA porogen extraction from extruded filaments.

| Sample ID | Fiber amt (g) | filament blend composition (nylon:PLA) | Obtained | % yield (expected yield) |
|---|---|---|---|---|
| 7895-126A | 1.94 g | 65:35 | 1.94 g | 100% (65%) |
| 7895-126B | 1.99 g | 60:40 | 1.80 g | 90% (60%) |
| 7895-126C | 1.84 g | 55:45 | 1.60 g | 87% (55%) |
| 7895-126D | 1.82 g | 50:50 | 1.59 g | 85% (50%) |

Example 6. Melt Extrusion of Polymeric Porogen Loaded Fibers

In this experiment, a general description of the process for melt-spinning the compounded nylon/PLA polymer porogen pellets into core/sheath or 15 wing bi-component fibers of approximately 20 micron diameters is provided.

The blended nylon/PLA pellets were melt spun into fibers using a bi-component fiber spinning machine. The bi-component fiber spinning machine is an LBS System from Hills Inc. (Melbourne, Fla.). The extruded fiber samples were core/sheath and 15 wing fibers with a sheath of PLA and the blended pellets in the core (or vice versa). Samples are summarized in Table 5 below.

TABLE 5

Summary table of extruded fibers containing polymeric porogens located within the fiber core or as a porogen-loaded external sheathing.

| Sample ID | Fiber type | Core blend composition (nylon:PLA) | Sheath composition | Core/Sheath ratio |
|---|---|---|---|---|
| 7895-122 core 2 | Core/Sheath | 80:20 | PLA | 50:50 |
| 7895-122 core 4 | Core/Sheath | 75:25 | PLA | 50:50 |
| 7895-128 core 4 | Core/Sheath | 65:35 | PLA | 50:50 |
| 7895-128 core 6 | Core/Sheath | 60:40 | PLA | 50:50 |
| 7895-128 core 7 | Core/Sheath | 55:45 | PLA | 50:50 |
| 7895-128 core 8 | Core/Sheath | 50:50 | PLA | 50:50 |
| 7895-123 core 6 | 15 wing | 70:30 | PLA | 1:2 |
| 7895-159 core 2 | Core/Sheath | 100:0 | nylon:PLA 60:40 | 50:50 |
| 7895-159 core 4 | Core/Sheath | 100:0 | nylon:PLA 60:40 | 2.6:1 |
| 7895-159 core 1 | Core/Sheath | 100:0 | nylon:PLA 60:40 | 8:1 |
| 7895-159 core 5 | Core/Sheath | 100:0 | nylon:PLA 60:40 | 1:2 |

Example 7. Melt Extrusion Using Hand-Blended Samples

In this experiment, a general description of the process for melt-spinning a hand-blended mixture of nylon and PLA polymer porogen pellets into core/sheath bi-component fibers of approximately 20 micron diameters is provided.

A variety of melt-extruded fiber samples were generated by melt spinning using a lab scale bi-component extruder from Hills Inc. (Melbourne, Fla.) mounted with a core/sheath spin pack. The sheath side of the die was fed with polylactic acid (PLA) pellets. For the core side of the die, polymer pellets were mixed at various ratios by simple agitation in a bag before being fed into the extruder. Fibers were drawn and wound on a core for later processing and analysis. Samples are summarized in Table 6 below.

TABLE 6

Summary table of extruded fibers containing hand-blended polymeric porogen/nylon mixtures located within the fiber core.

| Sample ID | Fiber type | Core hand-blend composition (nylon PA6:PLA) | Sheath composition | Core/Sheath ratio |
|---|---|---|---|---|
| 7993-6A | Core/Sheath | 30:70 | PLA | 50:50 |
| 7993-6B | Core/Sheath | 35:65 | PLA | 50:50 |
| 7993-6C | Core/Sheath | 40:60 | PLA | 50:50 |
| 7993-6D | Core/Sheath | 60:40 | PLA | 50:50 |
| 7993-6E | Core/Sheath | 65:35 | PLA | 50:50 |
| 7993-6F | Core/Sheath | 70:30 | PLA | 50:50 |

Example 8. General Procedure for PLA Extraction

In this experiment, the process for PLA porogen extraction from extruded bicomponent core/sheath fibers using a 1.5 N sodium hydroxide solution is described. The fibers are subsequently neutralized, washed, a gravimetric assay is performed, and the surfaces of the fibers are inspected by scanning electron microscopy (SEM). Kr BET surface area measurements are also conducted.

Figures 4A, 4B:
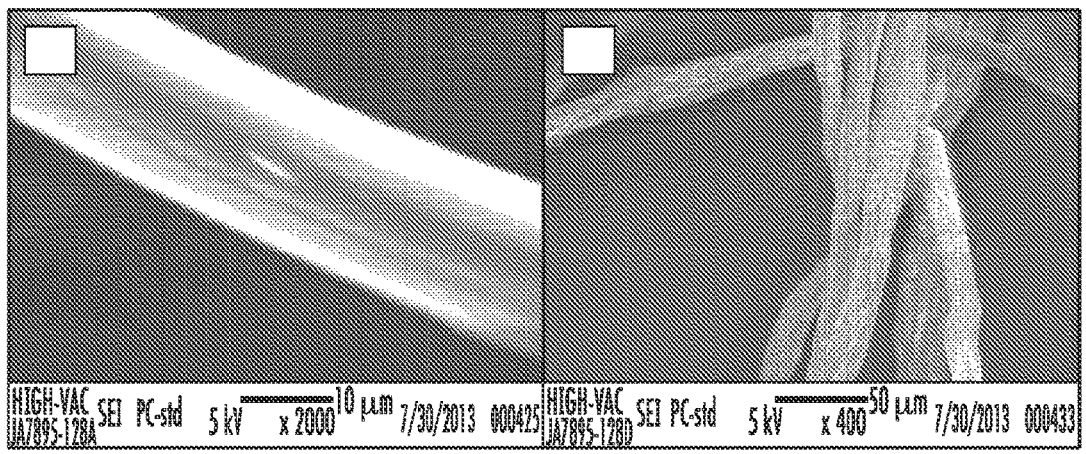
FIG. 4(a) is an SEM image after polymeric porogen and PLA sheath extraction of a core/sheath fiber with core blend composition nylon/PLA 65/35, 2000× magnification, in accordance with certain embodiments.
FIG. 4(b) is an SEM image after polymeric porogen and PLA sheath extraction of a core/sheath fiber with core blend composition nylon/PLA 60/40, 400× magnification, in accordance with certain embodiments.
Figures 4C, 4D:
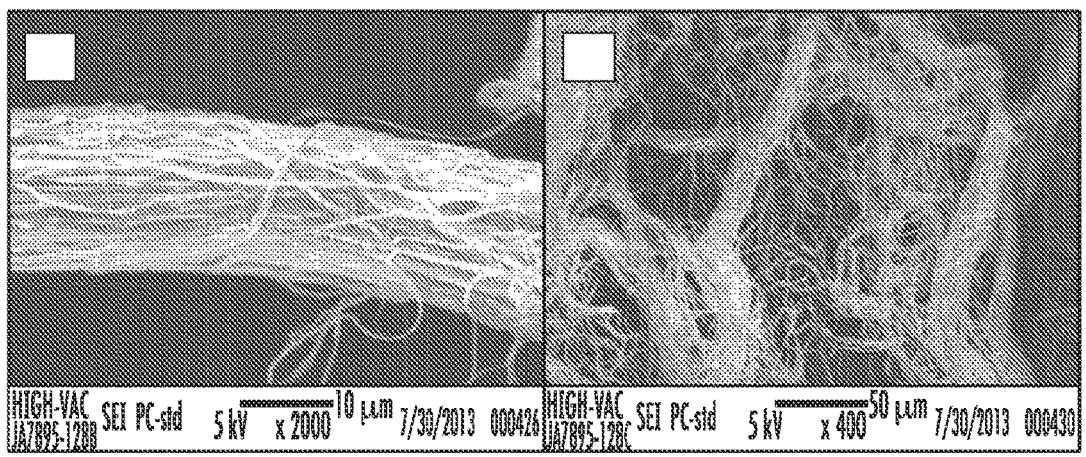
FIG. 4(c) is an SEM image after polymeric porogen and PLA sheath extraction of a core/sheath fiber with core blend composition nylon/PLA 55/45, 2000× magnification, in accordance with certain embodiments.
FIG. 4(d) is an SEM image after polymeric porogen and PLA sheath extraction of a core/sheath fiber with core blend composition nylon/PLA 50/50, 400× magnification, in accordance with certain embodiments.
Figure 5B:
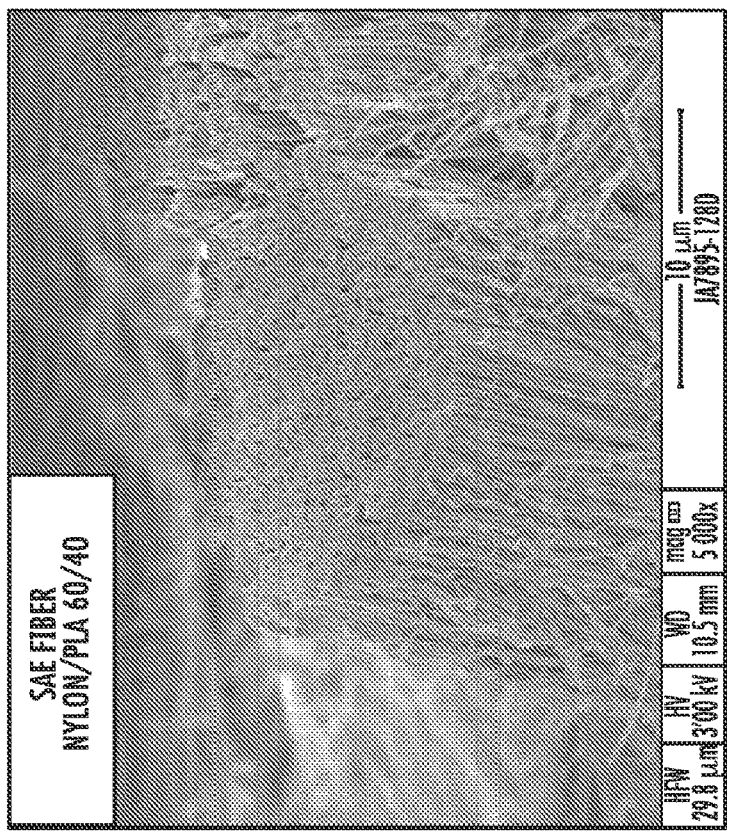
FIG. 5(b) is a cryo-SEM cross sectional image of a surface area enhanced (SAE) nylon/PLA 60/40 fiber in accordance with certain embodiments.
Figure 5A:
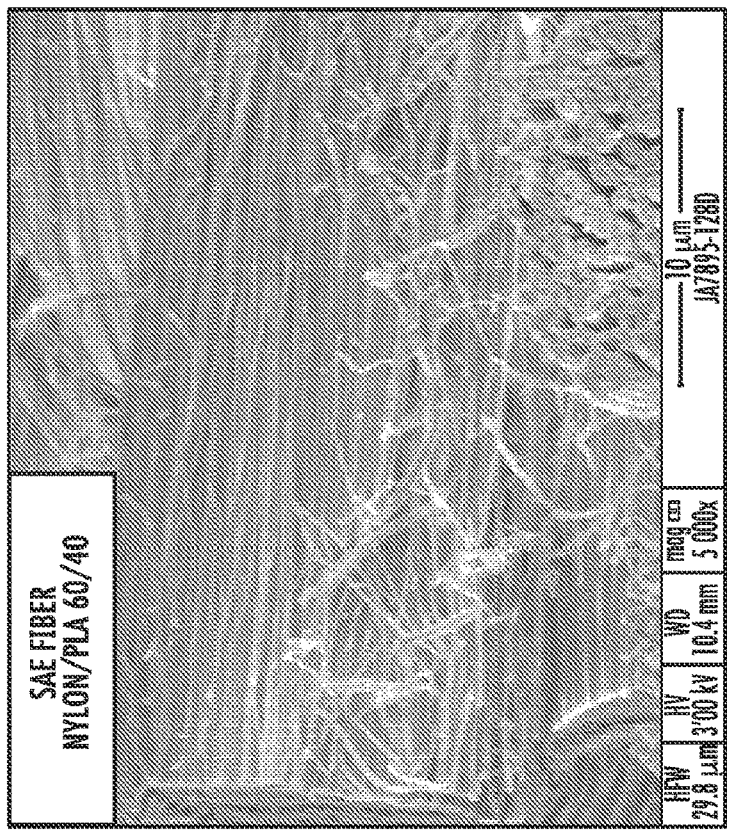
FIG. 5(a) is a cryo-SEM cross sectional image of a surface area enhanced (SAE) fiber in accordance with certain embodiments.
Figure 6:
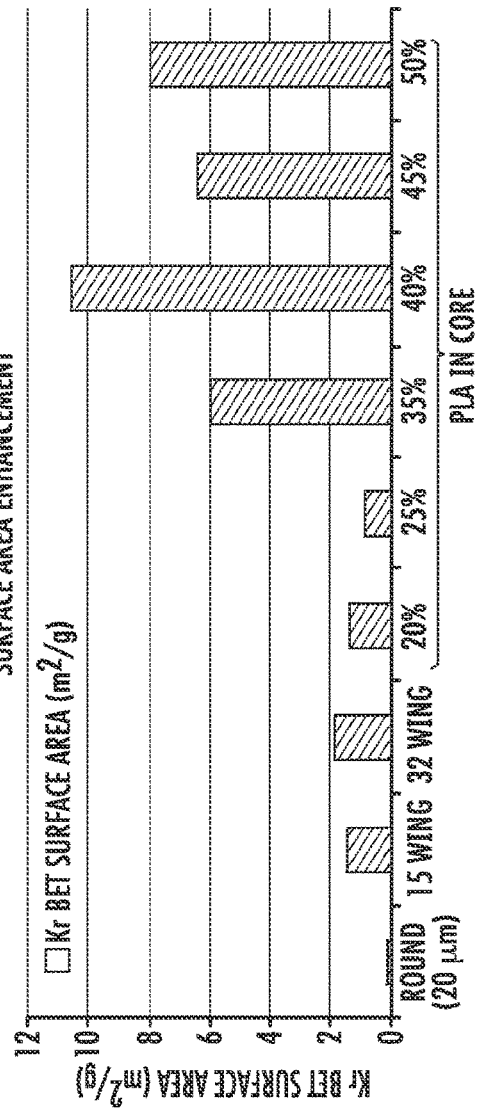
FIG. 6 is a graph of Kr BET surface area measurements for selected fibers in accordance with certain embodiments.

Into a 1 liter Pyrex bottle with cap were added 5.0 g of cut staple fiber (1.0 mm length) and 0.5 L of 1.5 N NaOH (0.75 mol). The suspension was stirred at room temperature overnight. The fiber solids were isolated by vacuum filtration and washed with DI water (3×250 mL) and ethanol (1×250 mL). The material was placed in an oven to dry at 60° C. for 18 hours. The results of the PLA polymeric porogen extraction experiments from extruded bi-component fibers (20 micron diameter) are shown in Table 7 below. From these data, we find that the PLA porogen was extracted from both the fiber sheath and from within the fiber core for all fiber samples. The small difference between the actual and expected yields is evidence of complete extraction of the PLA porogen from within the bi-component fiber. SEM inspection of the fiber surface morphology was conducted after extraction of the PLA polymeric porogen and these images are shown in FIG. 4. From these data, we find the appearance of a fibrillated surface morphology after PLA porogen extraction from the fibers with PLA loadings greater than 35 wt %. These fibers appear to be constructed of bundles of highly entangled nylon nanofibrils. For PLA porogen loadings greater than about 50 wt %, there is an apparent unraveling of the fiber structure to afford individual nylon nanofibers. Cryo-SEM cross section images for the 40 wt % PLA sample are shown in FIG. 5. From these cross section images, we find this fiber appears to be constructed of hundreds of loosely axially-aligned nylon nanofibrils and there is a significant porosity within the fiber cross section. Fibrillated surface morphologies such as these are expected to greatly increase the surface area of a fiber substrate. In FIG. 6, it is shown that high Kr BET surface areas are measured for the extracted nylon fiber samples that were constructed with PLA polymeric porogen loadings greater than 25 wt %.

TABLE 7

PLA porogen extraction and sheath removal.

| Sample ID | Fiber amt (g) | Core blend composition (nylon:PLA) | Sheath composition | Core/Sheath ratio | Obtained | % yield (expected yield) | Kr BET Surface area |
|---|---|---|---|---|---|---|---|
| 7895-128A | 5.0 g | 65:35 | PLA | 50:50 | 1.44 g | 29% (33%) | 6.08 m$^2$/g |
| 7895-128D | 5.0 g | 60:40 | PLA | 50:50 | 1.38 g | 28% (30%) | 10.57 m$^2$/g |
| 7895-128B | 5.0 g | 55:45 | PLA | 50:50 | 1.28 g | 26% (28%) | 6.39 m$^2$/g |
| 7895-128C | 5.0 g | 50:50 | PLA | 50:50 | 1.17 g | 23% (25%) | 8.07 m$^2$/g |

Example 9. Melt Extrusion of Winged Fibers Having a Porous Core

In this experiment, a general description of the process for melt-spinning the compounded nylon/PLA polymer porogen pellets into 15 wing bi-component fibers of approximately 15 micron diameters is provided. The PLA is subsequently extracted from the fiber sheath as well as from within the fiber core. As a result, these 15 wing fibers present a porous core structure.

Figures 7A, 7B:
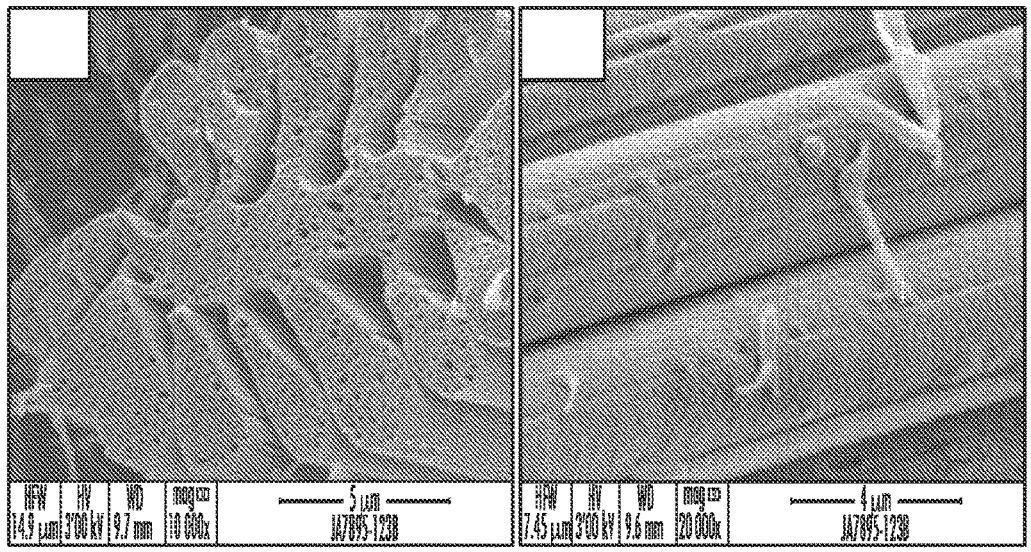
FIG. 7(a) is a cryo-SEM cross section image after polymeric porogen and PLA sheath extraction of a 15 wing fiber with core blend composition PA6/PLA 70/30, melt pump ratio S:C 2:1, 10000× magnification, in accordance with certain embodiments.
FIG. 7(b) is a cryo-SEM cross section image after polymeric porogen and PLA sheath extraction of a 15 wing fiber with core blend composition PA6/PLA 70/30, melt pump ratio S:C 2:1, 20000× magnification, in accordance with certain embodiments.
Figures 8A, 8B, 8C:
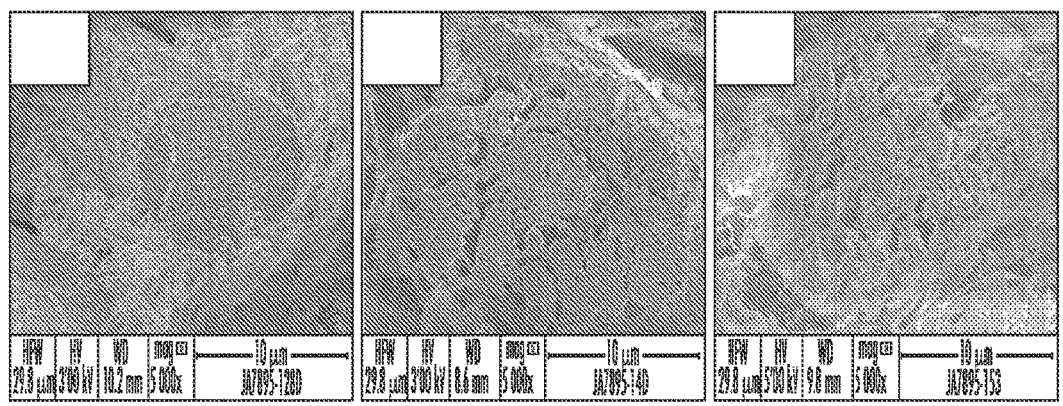
FIG. 8(a) is a cryo-SEM cross section image after polymeric porogen and PLA sheath extraction of a core/sheath fiber with core blend composition PA6/PLA 60/40, 5000× magnification, in accordance with certain embodiments.
FIG. 8(b) is a cryo-SEM cross section image after polymeric porogen and PLA sheath extraction of a 15 wing fiber with core blend composition PA6/PLA 60/40, melt pump ratio S:C 2:1, 5000× magnification, in accordance with certain embodiments.
FIG. 8(c) is a cryo-SEM cross section image after polymeric porogen and PLA sheath extraction of a 15 wing fiber with core blend composition PA6/PLA 60/40, melt pump ratio S:C 1:1, 5000× magnification, in accordance with certain embodiments.

The blended nylon/PLA pellets were melt spun into fibers using a bi-component fiber spinning machine. The bi-component fiber spinning machine is an LBS System from Hills Inc. (Melbourne, Fla.). The extruded fiber samples were 15 wing fibers and were prepared with a sheath of PLA and the blended pellets as the fiber core. After extraction of the PLA from the fiber sheath and from within the fiber core, a 15 wing fiber having a porous structure is provided. The general procedure for the extraction of the PLA polymeric porogen is described in the example above. Various 15 wing fiber samples prepared using nylon/PLA 70/30 and 60/40 blends as the fiber core composition are illustrated in FIG. 7 and FIG. 8. These images show the appearance of cylindrical pores or cavities that extend within the winged fiber cross sections. Such features are expected to further increase the surface area of winged fibers.

Example 10. General Procedure for the Surface Modification of SAE Fibers

In this experiment, a general procedure for the surface modification of SAE fibers with a pendant, strong cation exchange functional groups is described. This procedure involves the deposition of an epoxy-functional polymer coating onto the fiber surface, a heating step to covalently attach the polymer coating to the fiber surface, and a subsequent epoxy-ring opening process to install a sulfonic acid functionality onto the fiber surface.

Figure 9:
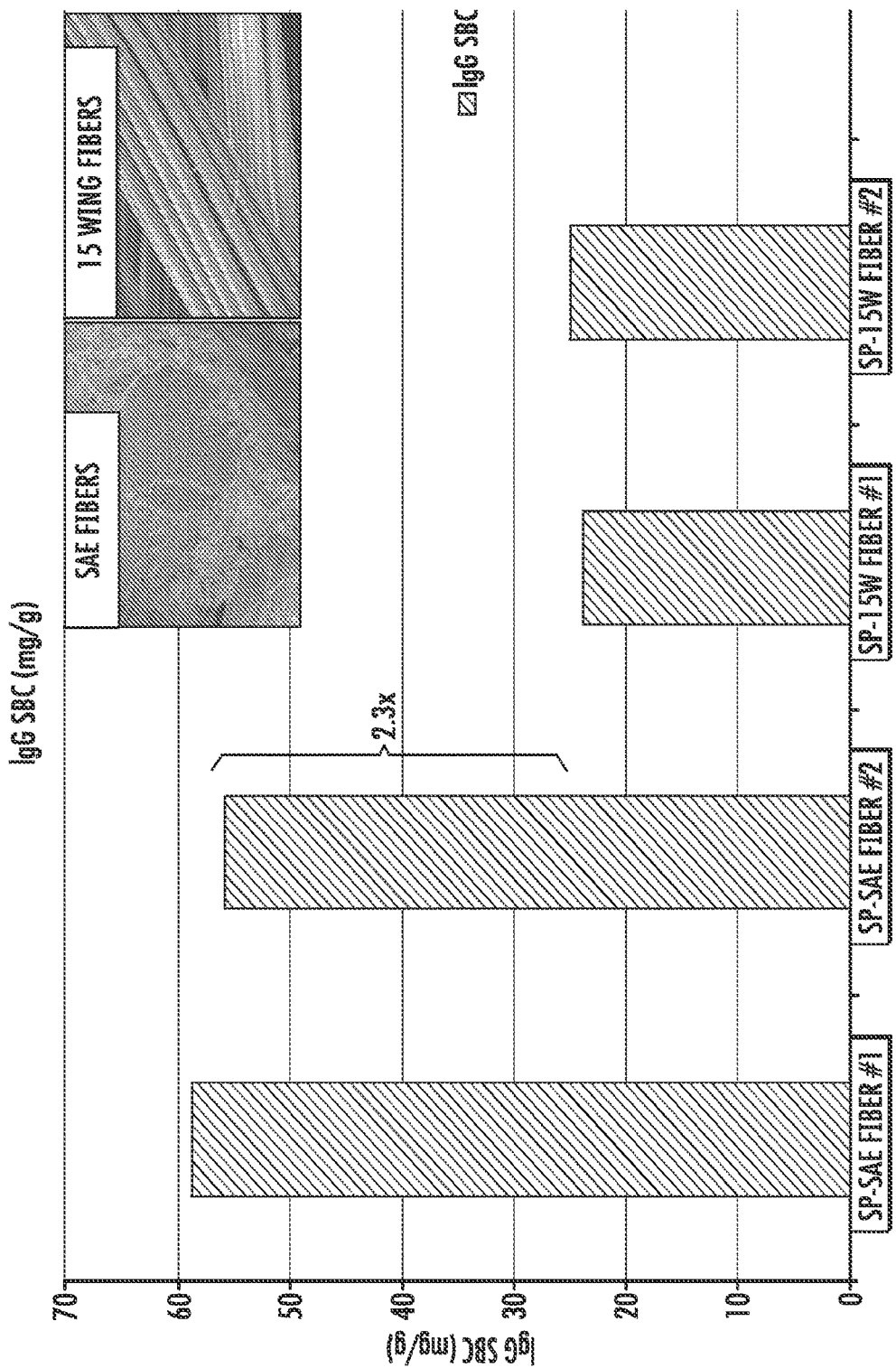
FIG. 9 is a graph of IgG SBC for SP surface modified SAE fibers (left) vs similarly modified SP 15 wing fibers (right), in accordance with certain embodiments.
Figure 10:
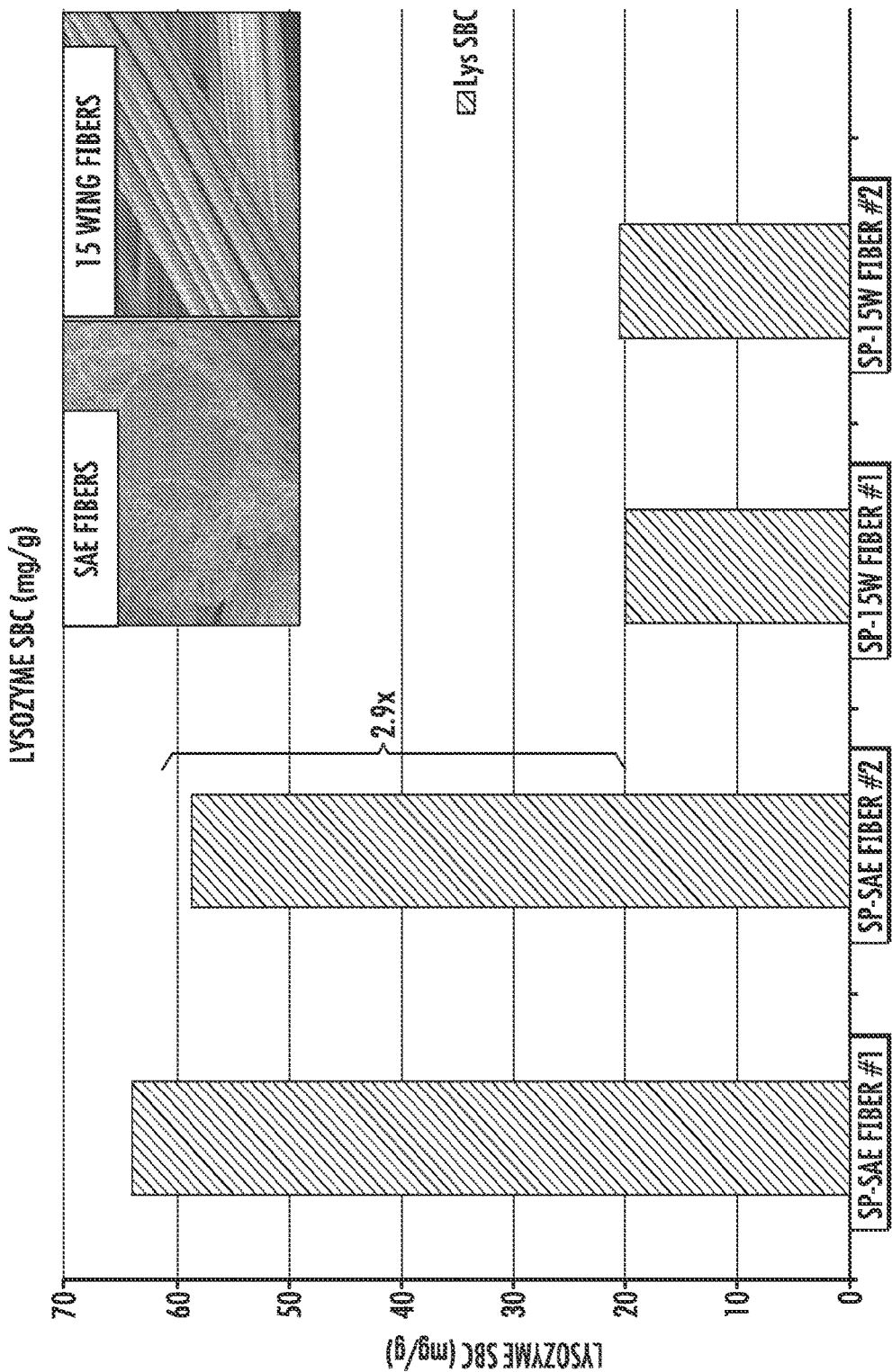
FIG. 10 is a graph of lysozyme SBC for SP surface modified SAE fibers (left) vs similarly modified SP 15 wing fibers (right), in accordance with certain embodiments.
Figure 11:
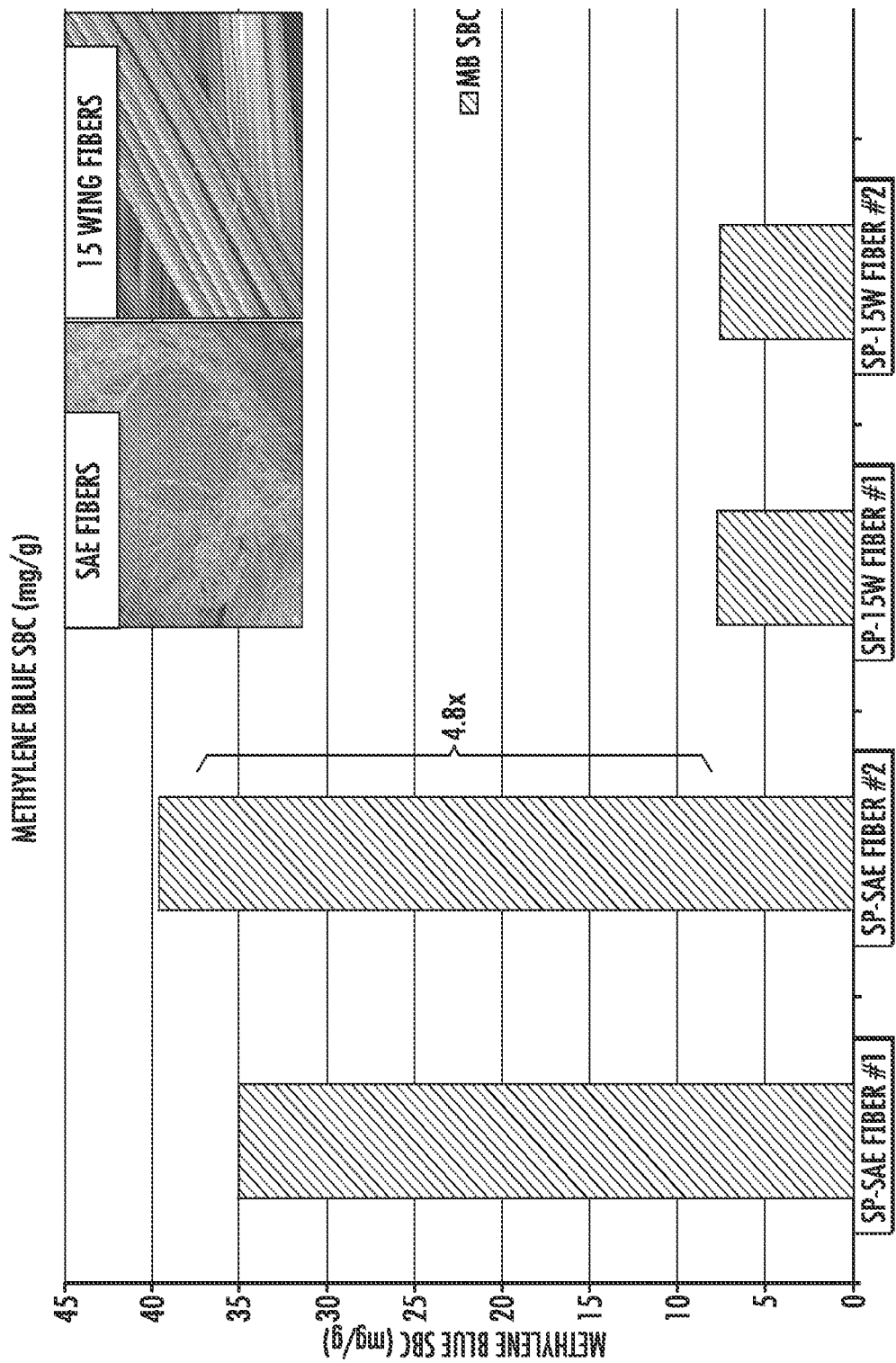
FIG. 11 is a graph of methylene blue SBC for SP surface modified SAE fibers (left) vs similarly modified SP 15 wing fibers (right), in accordance with certain embodiments.

Twenty-five grams of a 1 wt % solution of poly(glycidyl methacrylate) in methyl ethyl ketone (MEK) were prepared in a 30 mL glass vial. Into a separate 30 mL glass vial, were added 0.2 grams of fiber and 12.5 g of the 1% poly(glycidyl methacrylate) polymer solution. The suspension was agitated at room temperature overnight. The fiber solids were subsequently isolated by vacuum filtration and placed into an oven at 100° C. for 30 minutes. The fiber solids were removed from the oven and re-suspended in 40 mL MEK for 1 hour at room temperature. The fiber solids were isolated by vacuum filtration and then suspended in 15 mL of a 1 M sodium sulfite/0.4 M tetra-n-butyl ammonium bisulfate solution. The suspension was sparged with $N_2$ for 5 minutes, the vial sealed and heated to 80° C. overnight. The suspension was cooled to room temperature. The fiber solids were isolated by vacuum filtration and washed with DI water (5×30 mL), and ethanol (1×30 mL). The fibers were dried at 60° C. for 2 hours. Results for the surface modification of a surface area enhanced (SAE) core/sheath fiber as well as a non-porous 15 wing control sample are shown in Table 8 below. Static binding capacity measurements were also conducted for both of these sulfonic acid functionalized fibers using IgG, lysozyme, and methylene blue as large protein, small protein, and small molecule probes, respectively. Standard cation exchange binding conditions were employed for all of these static binding capacity tests and the results are summarized in FIGS. 9, 10, 11 and in Table 9 below. From these data, an increased static binding capacity for the SAE fiber over the 15 wing fiber is shown, as well as that the binding capacity advantage for the SAE fiber increases with decreasing molecular size.

TABLE 8

Surface modification of SAE nylon and 15 wing fibers, BET surface area, and recovery data.

| Sample ID | Fiber amt (g) | Fiber description | Kr BET Surface area | Obtained | % yield |
|---|---|---|---|---|---|
| 7895-179A | 0.20 g | SAE | 10.57 m²/g | 0.19 g | 95% |
| 7895-179B | 0.20 g | 15 wing | 1.43 m²/g | 0.17 g | 85% |

TABLE 9

Summary of static binding capacity data for SP modified SAE and 15 wing fibers.

|  | IgG | Lysozyme | Methylene Blue |
|---|---|---|---|
| Molecular weight | 160 KDa | 14.3 KDa | 374 Da |
| 15W fiber SBC (mg/g) | 25 | 21 | 8 |
| SAE fiber SBC (mg/g) | 58 | 62 | 38 |
| SAE fiber (SBC gain) | 2.3x | 2.9x | 4.8x |
| Est. accessible surface area[1] | 3.2 m²/g | 4.2 m²/g | 6.7 m²/g |
| % of BET surface area | 31% | 40% | 64% |

[1]Based on 15W fiber, 100% accessible surface area of 1.4 m²/g

Example 11. Surface Modification of SAE Fibers (7895-136)

In this experiment, a procedure for the modification of SAE type fibers with a surface-grafted ion exchange ligand for bind/elute cation exchange chromatography applications is described. The first step of this process involves the activation of the SAE fiber surface with a cross linked HPA/MBAm 95/5 polymer coating. This step provides a highly reactive hydroxyl-functional coating on the fiber surface that is well suited for a subsequent polymer grafting process. In a second step, the HPA/MBAm-modified fiber undergoes a ceric ion redox polymerization with 2-Acrylamido-2-methyl-1-propanesulfonic acid sodium salt to provide a polymer grafted fiber substrate. The grafted polymer provides pendant sulfonic acid functional groups for cation exchange chromatography applications.

SAE Nylon Fiber Surface Modification with HPA/MBAm 95/5.

Into a 500 mL Pyrex bottle were added hydroxypropylacrylate (HPA, 4.9 g, 38 mmol), N,N'-methylenebis(acrylamide) (MBAm, 0.28 g, 2 mmol) and water (253 mL). 6.0 g of surface area enhanced (SAE) nylon fibers were added to the mixture. Ammonium persulfate (0.63 g, 3 mmol) was added. The wet solids were heated to 80° C. for 4 hours.

After cooling to room temperature, the solids were transferred to a Buchner funnel and washed with hot water (4×200 mL) and ethanol (1×200 mL). The material was allowed to dry under vacuum for 20 minutes. The material was transferred to an oven and dried at 60° C. for 18 hours.

Obtained 6.46 g as white fibers.

Graft Polymerization of HPA/MBAm Modified Nylon Fibers.

Into 3×125 mL glass jars were added 2-Acrylamido-2-methyl-1-propanesulfonic acid sodium salt (AMPS-Na), water, HPA/MBAm modified SAE nylon fibers (see above) and 1 M HNO3 solution (in the amounts described in the table below). A 0.4 M solution of ammonium cerium(IV) nitrate (CAN) in 1 M HNO3 were added to each bottle. The reaction bottles were capped, sparged with nitrogen, and the mixtures were heated to 35° C. for 18 hours.

After cooling to room temperature, the solids were washed with a solution of 0.2 M ascorbic acid in 0.5 M sulfuric acid (3×80 mL), DI water (3×80 mL), 0.5 M sodium hydroxide solution (3×80 mL), DI water (3×80 mL) and ethanol (1×80 mL). The material was placed in an oven to dry at 60° C. for 18 hrs.

Obtained samples of a white fibrous solid (see table for recovery and weight add-on data).

The results of IgG dynamic binding capacity measurements for the SP-functionalized SAE fiber media of example 7895-136B are provided in Table 12 below. 1.0 g of the media was packed into an 11 mm internal diameter Vantage column and compressed to a bed depth of 3.0 cm (2.85 mL column volume, 0.35 g/mL fiber packing density). The packed fiber permeability at 0.35 g/mL was determined to be 200 mDa using 50 mM acetate buffer (pH 5). The dynamic binding capacity measurements were conducted over a range of linear velocities from 200 cm/hr to 60 cm/hr. These velocities correspond to residence times of 54 seconds to 3 minutes. The fiber media of example 7895-136B demonstrates IgG dynamic binding capacities in the range of 50 mg/mL.

TABLE 10

Cerium redox graft polymerization compositions and recovery data.

| Reaction # | HPA/MBAm fiber (g) | AMPS-Na monomer, g (mmol) | CAN (mM) | HNO3 (mM) | water (mL) | Product wt, g (% add-on) |
|---|---|---|---|---|---|---|
| 7895-136A | 1.5 g | 1.37 g (6 mmol) | 3 mM | 31 mM | 44 mL | 1.45 g (−3%) |
| 7895-136B | 1.5 g | 4.11 g (18 mmol) | 3 mM | 31 mM | 42 mL | 1.51 g (+1%) |
| 7895-136C | 1.5 g | 5.46 g (24 mmol) | 3 mM | 31 mM | 40 mL | 1.54 g (+3%) |

Example 12. Static Binding Capacity Measurement

In this experiment, the IgG static binding capacity of the SP surface-modified SAE fibers in a cation exchange mode is presented.

The results of IgG static binding capacity measurements for the SP-modified SAE nylon fibers are provided in Table 11 below. From these data, substantial IgG static binding capacities are shown for the SP surface-modified SAE fibers and these IgG SBC values are comparable to commercial bead-based cation exchange chromatography resins.

TABLE 11

IgG static binding capacity (SBC) data for SP modified SAE nylon fibers. Challenge: 2 g/L polyclonal human IgG (SeraCare Life Sciences, Milford, MA) in 50 mM Sodium Acetate (pH 5).

| Sample | Fiber Amt (mg) | IgG Bound (mg) | SBC (mg/g) | SBC (mg/mL)[1] |
|---|---|---|---|---|
| 7895-136A-1 | 56 | 8.0 | 143 | 47 |
| 7895-136A-2 | 32 | 4.6 | 143 | 47 |
| 7895-136B-1 | 44 | 8.1 | 185 | 61 |
| 7895-136B-2 | 59 | 10 | 177 | 58 |
| 7895-136C-1 | 62 | 12 | 197 | 65 |
| 7895-136C-2 | 69 | 4.2 | 61 | 20 |

[1]Based on a 0.33 g/mL fiber packing density

Example 13. Dynamic Binding Capacity Measurement

In this experiment, the packing of the SP surface-modified SAE fibers into a chromatography column and permeability of the packed fiber bed is described. The IgG dynamic binding capacity of the SP surface-modified SAE fibers in a cation exchange mode is also presented.

TABLE 12

IgG DBC values for the SP - functionalized SAE fiber cation-exchange media at 1, 5, 10, and 50% breakthrough at varying linear velocities (RT = residence time). Challenge: 2.0 g/L polyclonal human IgG (SeraCare Life Sciences, Milford, MA) in 50 mM acetate, pH 5.

| 7895-136B | DBC (mg/mL) | | | |
|---|---|---|---|---|
| % Breakthrough | 60 cm/hr (RT 180 sec) | 60 cm/hr (RT 180 sec) | 200 cm/hr (RT 54 sec) | 200 cm/hr (RT 54 sec) |
| 1 | 46 | 46 | 45 | 45 |
| 5 | 50 | 50 | 50 | 49 |
| 10 | 53 | 53 | 52 | 52 |
| 50 | 69 | 69 | 69 | 69 |

Example 14. Melt Extrusion of "Connected Islands in the Sea" (CIST) Fibers

In this experiment, a general description of the process for melt-spinning hand-blended mixtures of nylon and PLA polymer porogen pellets into 'connected islands in the sea" (CIST) type fibers of approximately 20 micron diameters is described. The fibers are subsequently neutralized, washed, a gravimetric assay is performed, and the surfaces of the fibers are inspected by scanning electron microscopy (SEM). $N_2$ BET surface area measurements are also conducted.

Figures 12A, 12B:
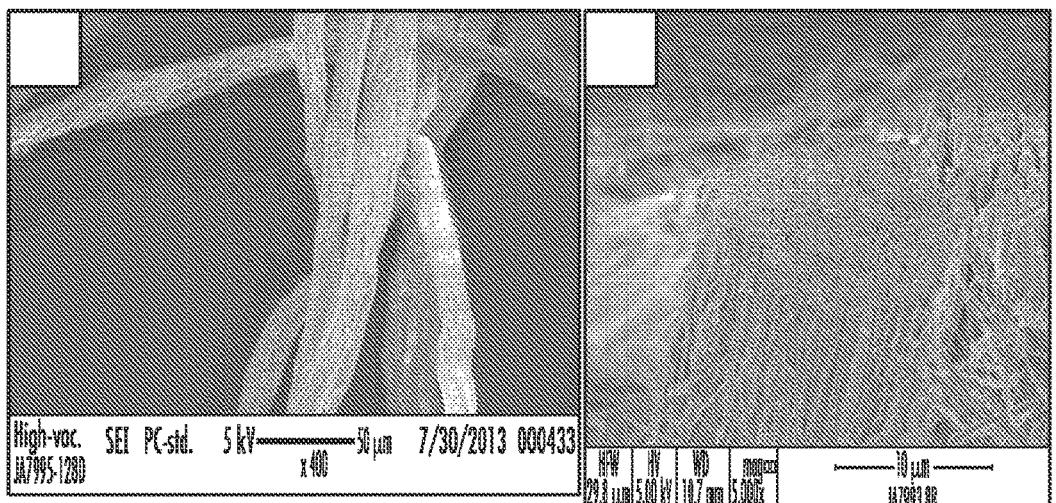
FIG. 12(a) is an SEM image of an SAE fiber with core blend composition nylon/PLA 60/40, 400× magnification, in accordance with certain embodiments.
FIG. 12(b) is a cryo-SEM cross sectional image of a SAE fiber with core blend composition nylon/PLA 60/40, 5000× magnification, in accordance with certain embodiments.
Figures 12C, 12D:
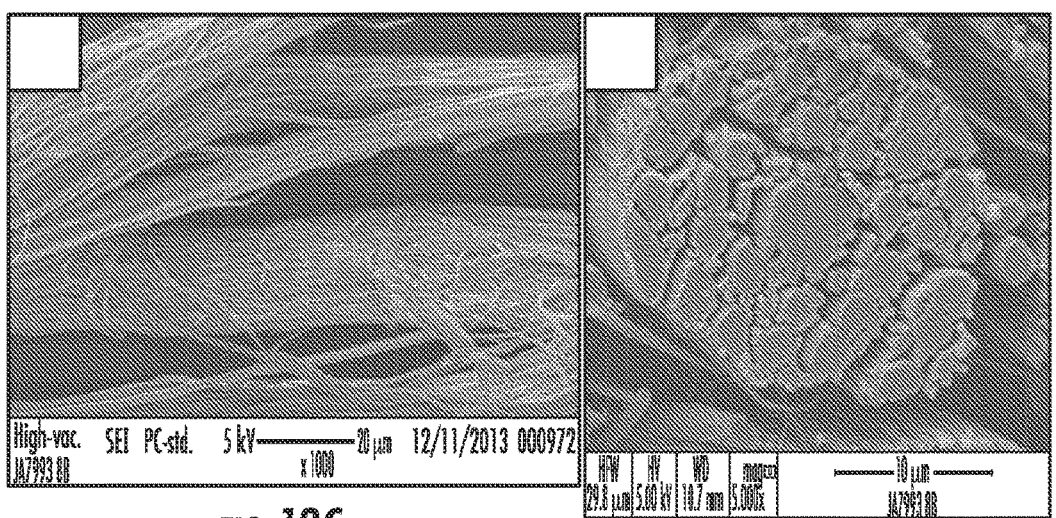
FIG. 12(c) is an SEM image of a CIST fiber with "island" composition nylon PA6 100/0, "sea" composition nylon/PLA 55/45, I/S ratio 1/1, 1000× magnification, in accordance with certain embodiments.
FIG. 12(d) is a cryo-SEM cross sectional image of a CIST fiber with "island" composition nylon PA6 100/0, "sea" composition nylon/PLA 55/45, I/S ratio 1/1, 5000× magnification, in accordance with certain embodiments.

A variety of melt-extruded fiber samples were generated by melt spinning using a lab scale bi-component extruder from Hills Inc. (Melbourne, Fla.) mounted with an "islands in the sea" spin pack (36 island configuration). The "island" side of the die was fed with nylon 6 pellets. For the "sea" side of the die, polymer pellets were mixed at various ratios by simple agitation in a bag before being fed into the extruder. For this example, the blend components were PLA and nylon 6. Fibers were drawn and wound on a core for later processing and analysis. Samples are summarized in the table below. After extraction of the PLA polymeric porogen from within the 'sea' domain of the extruded bi-component fiber, a CIST fiber having a porous structure is provided. Several examples of CIST type fibers are summarized in Table 14, below. The general procedure for the extraction of the PLA polymeric porogen is described in the example above. Various CIST fiber samples prepared using a range of nylon/PLA porogen blends as the fiber 'sea' domain composition were prepared. Surface and cryo-SEM cross section images of a CIST fiber and a SAE type fiber are provided in FIG. 12. From the cross section images, it can be seen that large channels or crevices extending throughout the interior of the CIST fiber and these features may make the internal surface considerably more accessible than for the SAE-type fiber. Such features are expected to improve the access of large proteins and biomolecules to the interior surface area of such nano-fibrillated fiber supports.

Example 15. Surface Modification of SAE, CIST, 15 Wing, and Round Nylon Fibers In this experiment, a procedure for the modification of SAE, CIST, and 15 wing type fibers with a surface-grafted ion exchange ligand for bind/elute cation exchange chromatography applications is described. In this process, the fiber surfaces are modified in a single step using a ceric ion redox polymerization with 3-sulfopropylmethacrylate potassium salt to provide a polymer-grafted fiber substrate. The grafted polymer provides pendant sulfonic acid functional groups for cation exchange chromatography applications.

Into a 125 mL bottle were added 3-sulfopropylmethacrylate potassium salt (3-SPMA), water, CIST nylon fibers and 1 M HNO3 solution (in the amounts described in the table below). A 0.4 M solution of ammonium cerium(IV) nitrate (CAN) in 1 M HNO3 was added to the bottle. The reaction bottle was capped and the mixture was heated to 35° C. for 5 hours.

After cooling to room temperature, the fiber solids from the bottle was washed with a solution of 0.2 M ascorbic acid in 0.5 M sulfuric acid (3×50 mL), DI water (3×50 mL), 0.5 M sodium hydroxide solution (3×50 mL), DI water (3×50 mL) and ethanol (1×50 mL). The material was placed in an oven to dry at 60° C. for 18 hrs.

Obtained samples of a white fibrous solid (see Table for recovery and weight add-on data).

TABLE 13

Summary table of extruded 'connected islands in the sea' (CIST) fibers containing 36 nylon PA6 'islands' and hand-blended polymeric porogen/nylon mixtures as the fiber 'sea' component.

| Sample ID | Fiber Type | Island Composition | Sea blend composition (nylon:PLA) | Island/Sea ratio |
|---|---|---|---|---|
| 7895-188D | CIST | PA6 | PA6:PLA 40:60 | 1:1 |
| 7895-188A | CIST | PA6 | PA6:PLA 60:40 | 3:2 |
| 7895-189D | CIST | PA6 | PA6:PLA 40:60 | 1:1 |
| 7895-189A | CIST | PA6 | PA6:PLA 60:40 | 1:1 |
| 7993-8A | CIST | PA6 | PA6:PLA 55:45 | 2.1:1 |
| 7993-8B | CIST | PA6 | PA6:PLA 55:45 | 1:1 |
| 7993-8C | CIST | PA6 | PA6:PLA 55:45 | 0.6:1 |
| 7993-8D | CIST | PA6 | PA6:PLA 60:40 | 2.1:1 |
| 7993-8E | CIST | PA6 | PA6:PLA 60:40 | 1:1 |
| 7993-8F | CIST | PA6 | PA6:PLA 60:40 | 0.6:1 |
|  | CIST | PA6 | PA6:PLA 65:35 | 2.1:1 |
|  | CIST | PA6 | PA6:PLA 65:35 | 1:1 |

TABLE 14

PLA porogen extraction and $N_2$ BET data for 'connected islands in the sea' (CIST) type fibers.

| Sample ID | Fiber Type | Fiber amt (g) | Island Composition | Sea blend composition (nylon:PLA) | Island/Sea ratio | Obtained | % yield (expected yield) | $N_2$ BET Surface area |
|---|---|---|---|---|---|---|---|---|
| 7895-188D | CIST | 10.5 g | nylon | nylon:PLA 40:60 | 1:1 | 6.9 g | 66% (70%) | 5.1 m$^2$/g |
| 7895-189A | CIST | 9.5 g | nylon (higher visc.) | nylon, higher visc.:PLA 60:40 | 1:1 | 7.6 g | 80% (80%) | 6.6 m$^2$/g |
| 7895-189D | CIST | 10.5 g | nylon | nylon, higher visc.:PLA 40:60 | 1:1 | 7.0 g | 67% (70%) | 4.4 m$^2$/g |

TABLE 15

Cerium redox graft polymerization compositions and recovery data for surface area enhanced (SAE), 'connected islands in the sea' (CIST), non-porous 15 wing and round control fibers (15 μm diameter).

| Reaction # | Fiber type | Fiber amt (g) | 3-SPMA monomer, g (mmol) | CAN (mM) | HNO3 (mM) | water (mL) | Product wt, g (% add-on) |
|---|---|---|---|---|---|---|---|
| 7895-142A | SAE | 1.5 g | 1.85 g (7.5 mmol) | 6 mM | 60 mM | 69.4 mL | 1.52 g, (+1%) |
| 7895-142B | SAE | 1.5 g | 4.62 g (19 mmol) | 6 mM | 60 mM | 69.4 mL | 1.68 g (+12%) |
| 7993-2A | CIST | 1.5 g | 1.85 g (7.5 mmol) | 6 mM | 60 mM | 69.4 mL | 1.50 g, (0%) |
| 7895-62D | 15 wing | 1.5 g | 9.24 g (38 mmol) | 6 mM | 60 mM | 69.4 mL | 1.8 g, (+19%) |
| 7895-142D | round, 15 μm | 1.5 g | 1.85 g (7.5 mmol) | 6 mM | 60 mM | 69.4 mL | 1.43 g, (−5%) |
| 7895-142E | round, 15 μm | 1.5 g | 4.62 g (19 mmol) | 6 mM | 60 mM | 69.4 mL | 1.50 g, (0%) |
| 7895-142F | round, 15 μm | 1.5 g | 9.24 g (38 mmol) | 6 mM | 60 mM | 69.4 mL | 1.52 g, (+1%) |

Example 16. Static Binding Capacity Measurement

In this experiment, the IgG static binding capacity of the SP surface-modified SAE, CIST, 15 wing, and simple round fibers in a cation exchange mode is presented. For the SAE fibers (samples #7895-142A and 7895-142B), we find that an increase in 3-SPMA monomer from 7.5 mmol to 19 mmol in the grafting step affords a substantial increase in IgG static binding capacity from 47 mg/g to 212 mg/g. The CIST fibers (entry 7993-2A-1, 7993-2A-2) give comparable IgG SBC values to the SAE type fibers at the low 3-SPMA monomer loading condition (7.5 mmol). The 15 wing fiber (entry 7895-62D) was modified using 38 mmol of 3-SPMA monomer and this sample affords an IgG SBC value of 130 mg/g. In comparison, simple 15 micron round fibers provide very low IgG SBC values under all of the grafting conditions evaluated. This may be attributed to the very low surface area of round fibers which lack projections or internal porous structures.

The results of IgG static binding capacity measurements for the SP modified surface area enhanced (SAE), 'connected islands in the sea' (CIST), non-porous 15 wing and round control fibers (15 μm diameter) are provided in Table 16 below.

TABLE 16

IgG static binding capacity data for SP modified surface area enhanced (SAE), 'connected islands in the sea' (CIST), non-porous 15 wing and round control fibers (15 μm diameter). Challenge: 2 g/L polyclonal human IgG (SeraCare Life Sciences, Milford, MA) in 50 mM Sodium Acetate (pH 5).

| Sample | Fiber type | Base fiber surface area (m2/g) | BET Method | Fiber Amt (mg) | IgG Bound (mg) | SBC (mg/g) |
|---|---|---|---|---|---|---|
| 7895-142A-1 | SAE | 10.6 | Kr BET, multipoint | 53 | 2.7 | 50 |
| 7895-142A-2 | SAE | 10.6 | Kr BET, multipoint | 74 | 3.3 | 45 |
| 7895-142B-1 | SAE | 10.6 | Kr BET, multipoint | 63 | 11 | 176 |
| 7895-142B-2 | SAE | 10.6 | Kr BET, multipoint | 54 | 13 | 248 |
| 7993-2A-1 | CIST | 4.4 | N2 BET, singlepoint | 49 | 2.7 | 56 |
| 7993-2A-2 | CIST | 4.4 | N2 BET, singlepoint | 61 | 2.9 | 48 |
| 7895-62D-1 | 15 wing | 1.43 | Kr BET, multipoint | 52 | 6.9 | 133 |
| 7895-62D-2 | 15 wing | 1.43 | Kr BET, multipoint | 51 | 6.4 | 125 |
| 7895-142F-1 | round, 15 μm | ~0.1 | Kr BET, multipoint | 68 | 0.5 | 7 |
| 7895-142F-2 | round, 15 μm | ~0.1 | Kr BET, multipoint | 51 | 0.7 | 13 |

Example 17. Melt-Extrusion of Shaped Fibers

Shaped fibers are prepared using a bi-component melt spinning process. The bi-component fiber has a core of one material and a sheath of a second polymer. These core and sheath materials could be any type of melt-processable thermoplastic known to those studied in the art. A series of die plates is used to split and redirect the two polymer feed streams into a given number of fibers and the desired cross-sectional shape. The fibers are drawn to the appropriate size after melt-spinning. The fiber characteristics are summarized in Table 17.

TABLE 17

Summary of shaped fiber shapes, BET surface area, and fiber diameter.

| Fiber Shape | BET Surface Area (m2/g) | Fiber Diameter (microns) |
|---|---|---|
| Fractal 1 | No Data | 14.8 |
| Fractal 2 | 2.11 | 15.1 |
| Snowflake | 1.25 | 26.9 |

Example 18. General Procedure for the Surface Modification of Shaped Fibers

The shaped fibers were prepared according to Example 10. See tables for IgG static binding capacity data.

TABLE 1817

Summary of static binding capacity data for SP modified Shaped and 15 wing fibers.

| Fiber Type | IgG SBC (mg/g) |
|---|---|
| 15W fiber SBC (mg/g) | 25 |
| Fractal 1 | NA |
| Fractal 2 | 90 |
| Snowflake | 29.5 |

Example 19. Surface Modification of Shaped Nylon Fibers

The shaped fibers were prepared according to Example 11. See table for recovery and weight add-on data.

TABLE 19

Cerium redox graft polymerization compositions and recovery data for fractal fiber.

| Reaction # | Fiber type | HPA/MBAm fiber (g) | AMPS-Na monomer, g (mmol) | CAN (mM) | HNO3 (mM) | water (mL) | Product wt, g (% add-on) |
|---|---|---|---|---|---|---|---|
| Ex. 19 | Fractal 2 | 1.51 g | 11.00 g (48 mmol) | 3 mM | 31 mM | 24.1 mL | 1.43 g (−5%) |

Example 20. Dynamic Binding Capacity Measurement

The surface modified fractal fibers from Example 19 above were packed according to the method described in Example 13.

The dynamic binding capacity measurements were conducted over a range of linear velocities from 200 cm/hr to 600 cm/hr. These velocities correspond to residence times of 54 seconds to 18 seconds. The fiber media of example 19 demonstrates IgG dynamic binding capacities in the range of 72 mg/mL.

TABLE 20

IgG DBC values for the SP - functionalized shaped fiber cation-exchange media at 1, 5, 10, and 50% breakthrough at varying linear velocities (RT = residence time). Challenge: 2.0 g/L polyclonal human IgG (SeraCare Life Sciences, Milford, MA) in 50 mM acetate, pH 5.

| Fiber: Ex 19 | DBC (mg/mL) | | | |
|---|---|---|---|---|
| % Breakthrough | 200 cm/hr (RT 54 sec) | 200 cm/hr (RT 54 sec) | 600 cm/hr (RT 18 sec) | 600 cm/hr (RT 18 sec) |
| 1 | 72 | 71 | 65 | 64 |
| 5 | 76 | 75 | 69 | 69 |
| 10 | 79 | 78 | 72 | 72 |
| 50 | 95 | 95 | 86 | 87 |

Example 21. Graft Polymerization of Un-Modified SAE Fibers

Surface modification of SAE fibers with a tetraalkylammonium (Q-type) polymeric ligand functionality for anion exchange chromatography (AEX) applications. Into a 500 mL bottle are added glycidyl methacrylate (GMA, 1.70 g, 12 mmol), and water (232.8 mL). 5 g of SAE fibers are added to the solution. 1 M $HNO_3$ solution (7.22 mL, 7.2 mmol) are added to the reaction mixture, followed by addition of a 0.4 M solution of ammonium cerium(IV) nitrate in 1 M $HNO_3$ (0.602 mL, 0.240 mmol).

The reaction mixture is heated to 35° C. for 1 hour.

After cooling to room temperature, the solids are washed with DI water (3×100 mL) and the damp material (12.21 g) is used immediately in the following step.

Q-Functionalization of Epoxy-Functionalized SAE Fibers.

Into a 250 mL bottle are added the damp GMA-functionalized SAE fibers from the example above, and a solution of 50 wt % trimethylamine (aq.) in methanol (in the amounts described in Table 21 below). The mixture is agitated at room temperature for 18 hours.

The fiber solids are subsequently washed with a solution of 0.2 M ascorbic acid in 0.5 M sulfuric acid (3×50 mL), DI water (3×50 mL), 1 M sodium hydroxide solution (3×50 mL), DI water (3×50 mL) and ethanol (1×50 mL). The material is placed in an oven to dry at 40° C. for 12 hrs.

Obtain samples of a white fibrous solid.

TABLE 21

Composition for the modification of epoxy-functionalized SAE fibers with trimethylamine.

| Reaction # | damp GMA-fiber (g) | 50% $Me_3N$, aq. (mL) | Methanol (mL) |
|---|---|---|---|
| Example 21 | 2.44 g | 50 mL | 50 mL |

Example 22. Graft Polymerization of Un-Modified SAE Fibers

Surface modification of SAE fibers with a poly(hydroxyethylmethacrylate) polymer functionality for hydrophobic interaction chromatography (HIC) applications. Into a 500 mL bottle are added hydroxyethylmethacrylate (HEMA, 1.69 g, 13 mmol), and water (232.5 mL). 5.00 g of SAE fibers are added to the solution. 1 M $HNO_3$ solution (7.21 mL, 7.2 mmol) are added to the reaction mixture, followed by addition of a 0.4 M solution of ammonium cerium(IV) nitrate in 1 M $HNO_3$ (0.601 mL, 0.240 mmol).

The reaction mixture is heated to 35° C. for 1 hour.

After cooling to room temperature, the solids are washed with a solution of 0.2 M ascorbic acid in 0.5 M sulfuric acid (3×100 mL), DI water (3×100 mL), 1 M sodium hydroxide solution (3×100 mL), DI water (3×100 mL) and ethanol (1×100 mL). The material is placed in an oven to dry at 40° C. for 12 hrs.

Example 23. SAE Fiber Surface Modification with Recombinant Protein A Affinity Ligand, rSPA Surface modification of SAE fibers with a recombinant protein A affinity ligand for affinity chromatography applications. Into a 250 mL bottle are added 1 M sodium bicarbonate (100 mL), recombinant protein A (rSPA #RN091139, 150 mg, as a 47.5 mg/mL solution in water) and water (90 mL). GMA-grafted SAE fibers (350 mg) from Example 21 above are added to the reaction mixture. The mixture is heated at 37° C. for 2.5 hours.

After cooling to room temperature, the solids are transferred to a Buchner funnel and washed with 0.1 M sodium bicarbonate (3×100 mL). The wet fiber solids are suspended in 100 mL of a 10 wt % thioglycerol solution in 0.2 M sodium bicarbonate/0.5 M sodium chloride solution. The mixture is stirred at room temperature overnight.

The solids are transferred to a Buchner funnel and washed with a solution of 0.1 M TRIZMA base with 0.15 M sodium chloride (1×75 mL), 0.05 M acetic acid solution (1×75 mL). The TRIZMA base and acetic acid washing cycles are repeated two additional times. The SAE fiber solids are finally washed with DI water (1×75 mL) and 20 wt % ethanol (1×75 mL). The SAE fiber solids are stored in 20 wt % ethanol solution.

Example 24. Poly(Allylamine) Modification of Epoxy-Functionalized Fibers

Surface modification of SAE fibers with a poly(allylamine) polymeric ligand functionality for anion exchange chromatography (AEX) applications. Into a 30 mL bottle are added GMA grafted SAE fibers from Example 21 above (0.5 g), water (10 mL), 40 wt % poly(allylamine) hydrochloride solution (1.25 g of 40 wt % solution) and 1.0 M sodium hydroxide (10 mL). The reaction mixture is heated to 35° C. for 18 hours.

After cooling to room temperature, the solids are washed with DI water (3×50 mL) and acetone (1×50 mL).

The damp material is placed in an oven to dry at 40° C. for 12 hrs.

Example 25. Flow-Through Host Cell Protein Clearance

The Q-functionalized SAE fiber media prepared according to Example 21 are evaluated for HCP removal activity in a flow-through polishing mode. 0.34 g of the Q-functionalized fiber media are packed into a 14.5 mm internal diameter column and compressed to a bed depth of 0.6 cm (1.00 mL column volume, 0.34 g/mL fiber packing density).

A cell culture media containing monoclonal antibody is clarified and then isolated using Protein A column chromatography and the pH of the solution is adjusted to pH 5. The pH of the Protein A elution is subsequently adjusted to pH 8 with TRIZMA base and then filtered through a 0.2 micron membrane.

The Q-functionalized SAE fiber media column is equilibrated with a buffer solution (25 mM Tris at pH 8). One hundred milliliters of 8.2 g/L monoclonal antibody Protein A elution (pH 8) are passed through the column at a flow rate of 1.0 mL/min. Ten 10 mL factions are collected. Bound HCP is eluted using a 1 M sodium chloride solution in 25 mM Tris pH 8 as an elution buffer. Two 10 mL elution fractions are also collected. The ten flow-through fractions and two elution fractions are analyzed by HCP-ELISA and protein A HPLC to determine the level of HCP clearance and the monoclonal antibody recovery, respectively.

Example 26. SAE Fiber Media Capability for the Bind/Elute Purification of Viruses Static binding capacity and elution recovery experiments for bacteriophage φ6 are conducted as shown below. Anion exchange mode bind/elute operations also may be performed in a packed column format according to procedures similar to those described in Example 13. Into 5 plastic centrifuge tubes are added the Q-functionalized SAE fiber media of Example 21. Each of the SAE fiber samples are equilibrated with 5 mL of 25 mM Tris buffer (pH 8, with 0.18 mg/mL HSA) with agitation for 10 minutes. The tubes are spun at room temperature in a table top centrifuge at 4000 rpm for 10 minutes to pellet the SAE fiber media. 2.5 mL of the supernatant are removed and 2.5 mL of a $1.7 \times 10^7$ pfu/mL φ6 solution in 25 mM Tris buffer (pH 8, with 0.18 mg/mL HSA) are added to each tube. The samples are agitated at room temperature for 1 hour. Afterwards, the tubes are spun at room temperature in a table top centrifuge at 4000 rpm for 15 minutes to pellet the SAE fiber media. 2.5 mL of the supernatant are removed and these samples are assayed for unbound φ6 by plaque-forming assay. The tubes are washed 3 times with 2.5 mL washings of 25 mM Tris buffer (pH 8, with 0.18 mg/mL HSA) with centrifugation to pellet the SAE fiber media in between each wash and removal of 2.5 mL of the supernatant. After washing, 2.5 mL of a 1.0 M NaCl solution in 25 mM Tris buffer (pH 8, with 0.18 mg/mL HSA) are added to each tube (5 mL total volume, final NaCl concentration is 0.5 M). The samples are agitated at room temperature for 10 minutes. Afterwards, the tubes are spun at room temperature in a table top centrifuge at 4000 rpm for 10 minutes to pellet the SAE fiber media. 2.5 mL of the supernatant are removed and these elution samples are assayed for eluted φ6 by plaque forming assay. The Q-functionalized SAE fiber media can be integrated into a prepacked device format or a chromatography column for flow-through viral clearance or bind/elute viral purification applications.

What is claimed is:

1. A method of purifying a biomolecule in a sample, comprising contacting said sample with a bed of porous entangled nanofibers, made by a melt extrusion of a blend of polymer and porogen and drawing to a target diameter and extracting porogen therefrom, each of said porous entangled nanofibers within said bed having a diameter less than or equal to 1 micron, said porous entangled nanofibers arranged in discrete porous bundles, said porous entangled nanofibers having imparted thereon functionality enabling chromatography.

2. The method of claim 1, wherein said biomolecule comprises a virus.

3. The method of claim 1, wherein said functionality is grafted to said nanofibers.

4. The method of claim 1, wherein said functionality enables purification in a bind/elute mode.

5. The method of claim 1, wherein said polymer is a melt-processable thermoplastic polymer.

6. The method of claim 5, wherein said melt-processable thermoplastic polymer is selected from the group consisting of polyamides, polyolefins, polyvinyl chloride, polystyrene, poly methylmethacrylate, polylactic acid, polyester, polyethylene terephthalate, polybutylene terephthalate, polyetherurethanes, polyvinyl alcohol, polyimide, polycarbonate, polyetheretherketone, polysulfone, and polytrimethylene terephthalate.

7. The method of claim 1, wherein said polymer is nylon.

8. The method of claim 1, wherein said porogen is a polymeric porogen.

9. The method of claim 8, wherein said polymeric porogen is poly(lactic acid).

10. The method of claim 1, wherein said porogen is a mineral porogen.

11. The method of claim 1, wherein said porogen is a combination of a polymeric porogen and a mineral porogen.

* * * * *